US012807935B2

(12) United States Patent
McKnight

(10) Patent No.: US 12,807,935 B2
(45) Date of Patent: Nov. 24, 2026

(54) METHODS AND COMPOSITIONS FOR ASSESSING PROTEIN FUNCTION

(71) Applicant: University of Oregon, Eugene, OR (US)

(72) Inventor: Jeffrey McKnight, Eugene, OR (US)

(73) Assignee: University of Oregon, Eugene, OR (US)

( * ) Notice: Subject to any disclaimer, the term of this patent is extended or adjusted under 35 U.S.C. 154(b) by 1335 days.

(21) Appl. No.: 17/589,081

(22) Filed: Jan. 31, 2022

(65) Prior Publication Data

US 2022/0154167 A1 May 19, 2022

Related U.S. Application Data

(62) Division of application No. 16/910,507, filed on Jun. 24, 2020, now Pat. No. 11,236,326.

(60) Provisional application No. 62/868,753, filed on Jun. 28, 2019.

(51) Int. Cl.
*C12N 15/10* (2006.01)
*C07K 14/315* (2006.01)
*C12N 9/22* (2006.01)
*C12N 15/63* (2006.01)

(52) U.S. Cl.
CPC .......... *C12N 15/102* (2013.01); *C07K 14/315* (2013.01); *C12N 9/22* (2013.01); *C12N 15/63* (2013.01)

(58) Field of Classification Search
None
See application file for complete search history.

(56) References Cited

U.S. PATENT DOCUMENTS

| | | | | |
|---|---|---|---|---|
| 9,547,003 | B2 | 1/2017 | Howarth | |
| 10,247,727 | B2 | 4/2019 | Howarth | |
| 10,527,609 | B2 | 1/2020 | Howarth | |
| 11,453,883 | B2 * | 9/2022 | Ylera | C07K 16/241 |
| 12,275,762 | B2 * | 4/2025 | Howarth | C07K 1/14 |
| 2013/0053544 | A1 * | 2/2013 | Howarth | C07K 14/315 435/254.2 |

FOREIGN PATENT DOCUMENTS

| | | |
|---|---|---|
| WO | WO 2011/098772 | 8/2011 |
| WO | WO 2017/023974 | 2/2017 |
| WO | WO 2020/198151 A1 | 10/2020 |

OTHER PUBLICATIONS

Reddington et al., "Secrets of a covalent interaction for biomaterials and biotechnology: SpyTag and SpyCatcher" 29 Current Opinion in Chemical Biology 94-99 (Year: 2015).*

Dovala et al., "Rapid analysis of protein expression and solubility with the SpyTag-SpyCatcher system" 117 Protein Expression and Purification 44-51 (Year: 2016).*

Dang et al., "SNAC-tag for Sequence-specific Chemical Protein Cleavage," *Nat Methods*, vol. 16, No. 4, pp. 319-322, 2019 (Author Manuscript version, 12 pages).

Donovan et al., "Engineered Chromatin Remodeling Proteins for Precise Nucleosome Positioning," *Cell Reports* vol. 29, pp. 2520-2535, 2019.

Hatlem et al., "Catching a SPY: Using the SpyCatcher-SpyTab and Related Systems for Labeling and Localizing Bacterial Proteins," *International Journal of Molecular Sciences*, 20:2129, 2019 (19 pages).

Kaya-Okur et al., "CUT&Tag for efficient epigenomic profiling of small samples and single cells," *Nat. Commun.* 10:1930, 2019 (10 pages).

Khairil Anuar et al. "Spy&Go purification of SpyTag-proteins using pseudo-SpyCatcher to access an oligomerization toolbox," *Nature Communications*, 10:1734, 2019 (13 pages).

Li et al., "Structural Analysis and Optimization of the Covalent Association between SpyCatcher and a Peptide Tag," *Journal of Molecular Biology*, vol. 426, pp. 309-317, 2014.

Lim et al., "CRISPR/Cas-directed programmable assembly of multi-enzyme complexes," *Chem. Commun.* vol. 56, pp. 4950-4953, 2020.

Zakeri et al., "Peptide tag forming a rapid covalent bond to a protein, through engineering a bacterial adhesin," *Proceedings of the National Academy of Sciences*, vol. 109, No. 12, pp. E690-E697, 2012.

Zhao et al., "SpyCLIP: an easy-to-use and high-throughput compatible CLIP platform for the characterization of protein-RNA interactions with high accuracy," *Nucleic Acids Research*, vol. 47, No. 6, e33, 2019 (12 pages).

* cited by examiner

*Primary Examiner* — Nancy J Leith
(74) *Attorney, Agent, or Firm* — Klarquist Sparkman, LLP

(57) ABSTRACT

Compositions and methods for assessing protein function are provided. A modified SpyCatcher protein that can include a tag is provided. Modified SpyCatcher proteins linked to a protein of interest, such as a nuclease are also provided. The methods include contacting a SpyCatcher protein and a SpyTagged protein to form a complex that may further include a protein of interest, one or more nucleic acids, and/or a nuclease. The methods can be used to purify a protein of interest or identify or target a protein binding site in a nucleic acid.

7 Claims, 10 Drawing Sheets

Specification includes a Sequence Listing.

FIG. 12A
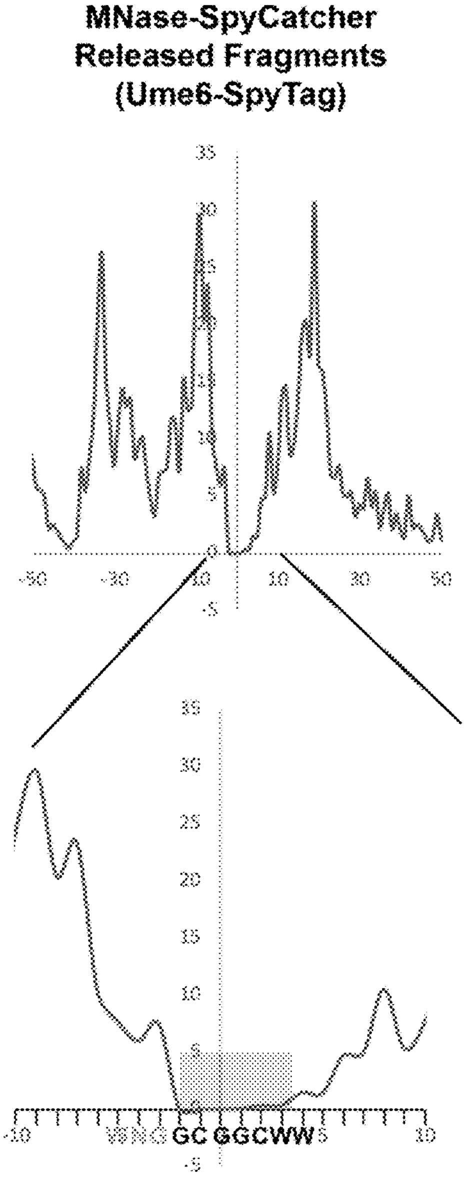
FIG. 12B
FIG. 12C
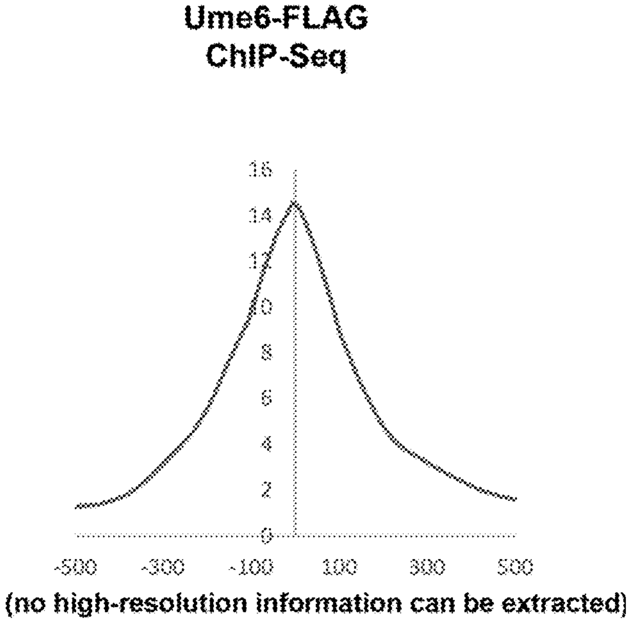

METHODS AND COMPOSITIONS FOR ASSESSING PROTEIN FUNCTION

CROSS REFERENCE TO RELATED APPLICATIONS

This application is a divisional of U.S. application Ser. No. 16/910,507, filed Jun. 24, 2020, which in turn claims the benefit of U.S. Provisional Application No. 62/868,753, filed Jun. 28, 2019, both of which are incorporated herein by reference in their entirety.

ACKNOWLEDGMENT OF GOVERNMENT SUPPORT

This invention was made with government support under grant number R01 GM129242 awarded by the National Institutes of Health. The government has certain rights in the invention.

FIELD

This disclosure relates to methods and compositions for assessing protein function, particularly methods of protein purification, methods for mapping protein-DNA binding, and methods to localize proteins to a selected genomic location.

BACKGROUND

Protein studies are universal across disciplines in biological sciences. Because of this ubiquity, numerous strategies exist to purify, localize, redirect, deplete, and visualize proteins in all model organisms. However, it can be cumbersome to create required strains to investigate the many different aspects of protein function. Even in yeast, one of the "simplest" model organisms, there is no streamlined approach that allows for robust protein localization and purification from a single strain. Instead, there are a host of unique N- and C-terminal tags that can be added for different desired applications.

SUMMARY

Disclosed herein is a unified approach that can be used to assess many aspects of protein function, providing advantages such as speed, simplicity, and efficiency across multiple fields.

In some embodiments, a modified SpyCatcher polypeptide including at least one heterologous cysteine residue is provided. In some examples, the modified SpyCatcher polypeptide includes a cysteine at an amino acid residue corresponding to amino acid position 50 of SEQ ID NO: 6. The modified SpyCatcher polypeptide in some examples, includes an amino acid sequence having at least 95% sequence identity to SEQ ID NO: 7, an amino acid sequence including SEQ ID NO: 7, or an amino acid sequence consisting of SEQ ID NO: 7.

In some embodiments, a modified SpyCatcher polypeptide provided herein includes a tag covalently linked to the cysteine residue. In some non-limiting examples, the tag is biotin. In additional embodiments, the modified SpyCatcher polypeptide is also covalently linked to a protein of interest. In non-limiting examples, the protein of interest is a nuclease, such as a micrococcal nuclease or a catalytically inactive Cas9 nuclease (e.g., dCas9). In other examples, the protein of interest is Tn5 transposase.

Nucleic acids encoding the modified SpyCatcher polypeptides are also provided. In some examples, the nucleic acid includes a nucleic acid sequence with at least 95% sequence identity to SEQ ID NO: 10 or SEQ ID NO: 13, a nucleic acid sequence including SEQ ID NO: 10 or SEQ ID NO: 13, or a nucleic acid sequence consisting of SEQ ID NO: 10 or SEQ ID NO: 13. Also provided are vectors including nucleic acids encoding the modified SpyCatcher polypeptides disclosed herein. In one non-limiting example, the vector includes the nucleic acid sequence of SEQ ID NO: 12.

Kits including the modified SpyCatcher polypeptides or nucleic acids encoding the modified SpyCatcher polypeptides are also provided. In some examples, the kits further include a SpyTag or SpyTag-SNAC tag polypeptide or a nucleic acid encoding the SpyTag or SpyTag-SNAC tag polypeptide.

In some embodiments, methods of purifying a protein of interest are provided. In some examples, the methods include contacting a SpyCatcher polypeptide including a tag covalently linked to a heterologous cysteine residue with a protein of interest covalently linked to a SpyTag polypeptide or a SpyTag-SNAC tag polypeptide, under conditions sufficient for the SpyCatcher polypeptide and the SpyTag polypeptide or SpyTag-SNAC tag polypeptide to form a covalently bound SpyCatcher-SpyTag-protein of interest complex or a SpyCatcher-SpyTag-SNAC tag-protein of interest complex, and contacting the SpyCatcher-SpyTag-protein of interest complex or SpyCatcher-SpyTag-SNAC tag-protein of interest complex with a binding partner for the tag covalently linked to the SpyCatcher polypeptide under conditions sufficient for the binding partner to bind to the tag. The complex is washed one or more times, the SpyTag or SpyTag-SNAC tag is cleaved from the complex, and the protein of interest is isolated. In some examples, contacting the SpyCatcher polypeptide with the protein of interest covalently linked to the SpyTag polypeptide or the SpyTag-SNAC tag polypeptide is performed in a lysate of a cell expressing the protein of interest covalently linked to the SpyTag polypeptide or the SpyTag-SNAC tag polypeptide. In one non-limiting example, the tag on the modified SpyCatcher polypeptide is biotin, and the binding partner for the tag is streptavidin.

In other embodiments, methods of mapping protein binding to a nucleic acid are provided. In some examples, the methods include contacting a modified SpyCatcher polypeptide including a tag covalently linked to a heterologous cysteine residue with a protein of interest covalently linked to a SpyTag polypeptide or a SpyTag-SNAC tag polypeptide and a population of nucleic acids under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex and contacting the SpyCatcher-SpyTag-protein-nucleic acid complex or SpyCatcher-SpyTag-SNAC tag-protein-nucleic acid complex with a binding partner for the tag covalently linked to the SpyCatcher polypeptide under conditions sufficient for the binding partner to bind to the tag. The complex is contacted with a nuclease under conditions sufficient for the nuclease to cleave the nucleic acid flanking the complex and the complex is washed one or more times. The SpyCatcher-SpyTag-protein or SpyCatcher-SpyTag-SNAC tag-protein is dissociated from the nucleic acid; and the nucleic acid is isolated. In some examples, contacting the modified SpyCatcher polypeptide with the protein of interest covalently linked to the SpyTag polypeptide or the SpyTag-SNAC tag polypeptide and the population of nucleic acids is performed in a permeabilized cell expressing the protein of interest covalently linked to the SpyTag polypeptide or the SpyTag-SNAC tag polypeptide. In one non-limiting example, the tag on the modified SpyCatcher polypeptide is biotin, and the binding partner for the tag is streptavidin. In some examples, the methods further include identifying the isolated nucleic acid.

In another embodiment, the methods include contacting a SpyCatcher polypeptide covalently linked to a micrococcal nuclease with a protein of interest covalently linked to a SpyTag polypeptide or a SpyTag-SNAC tag polypeptide and a population of nucleic acids, under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex and incubating the SpyCatcher-SpyTag-protein-nucleic acid complex or the SpyCatcher-SpyTag-SNAC tag-protein-nucleic acid complex under conditions sufficient to activate the micrococcal nuclease. The complex is washed one or more times, the SpyCatcher-SpyTag or SpyCatcher-SpyTag-SNAC tag is dissociated from the nucleic acid, and the nucleic acid is isolated. In some examples, contacting the SpyCatcher polypeptide with the protein of interest covalently linked to the SpyTag polypeptide or the SpyTag-SNAC tag polypeptide is performed in a permeabilized cell expressing the protein of interest covalently linked to the SpyTag polypeptide or the SpyTag-SNAC tag polypeptide or in a permeabilized cell co-expressing the SpyCatcher polypeptide and the protein of interest covalently linked to the SpyTag polypeptide or the SpyTag-SNAC tag polypeptide. In some examples, the method also includes identifying the isolated nucleic acid. In additional examples, the SpyCatcher polypeptide covalently linked to the micrococcal nuclease also includes a tag linked to a heterologous cysteine in the SpyCatcher polypeptide.

In a still further embodiment, the methods include a SpyCatcher polypeptide covalently linked to a Tn5 transposase with a protein of interest covalently linked to a SpyTag polypeptide or a SpyTag-SNAC tag polypeptide and a population of nucleic acids, under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex, and incubating the SpyCatcher-SpyTag-protein-nucleic acid complex or the SpyCatcher-SpyTag-SNAC tag-protein-nucleic acid complex under conditions sufficient to activate the Tn5 transposase. The complex is washed one or more times, the SpyCatcher-SpyTag or SpyCatcher-SpyTag-SNAC tag is dissociated from the nucleic acid, and the nucleic acid is isolated. In some examples, contacting the SpyCatcher polypeptide with the protein of interest covalently linked to the SpyTag polypeptide or the SpyTag-SNAC tag polypeptide is performed in a permeabilized cell expressing the protein of interest covalently linked to the SpyTag polypeptide or the SpyTag-SNAC tag polypeptide or in a permeabilized cell co-expressing the SpyCatcher polypeptide and the protein of interest covalently linked to the SpyTag polypeptide or the SpyTag-SNAC tag polypeptide. In some examples, the method also includes identifying the isolated nucleic acid. In additional examples, the SpyCatcher polypeptide covalently linked to the Tn5 transposase also includes a tag linked to a heterologous cysteine in the SpyCatcher polypeptide.

Also provided are methods of localizing a protein to a nucleic acid. In some embodiments, the methods include contacting a SpyCatcher polypeptide covalently linked to a dCas9 nuclease with a protein of interest covalently linked to a SpyTag polypeptide or a SpyTag-SNAC tag polypeptide, a guide RNA specific for a target nucleic acid, and a population of nucleic acids under conditions sufficient for the SpyCatcher polypeptide and the SpyTag polypeptide or SpyTag-SNAC tag polypeptide and nucleic acids to form a SpyCatcher-SpyTag-protein-gRNA-nucleic acid complex or a SpyCatcher-SpyTag-SNAC tag-protein-gRNA-nucleic acid complex. In some examples, the methods also include analyzing the target nucleic acid. In additional examples, the SpyCatcher polypeptide covalently linked to the dCas9 also includes a tag linked to a heterologous cysteine in the SpyCatcher polypeptide.

The foregoing and other features of the disclosure will become more apparent from the following detailed description, which proceeds with reference to the accompanying figures.

BRIEF DESCRIPTION OF THE DRAWINGS

FIGS. 12A-12C show high resolution Ume6 footprint from pooled analysis of data from all 202 intergenic Ume6 binding motifs. FIG. 12A shows characteristic cutting on both sides of motif, with no cutting in the nucleotides wherein the mapped protein sits. FIG. 12B shows a magnified view of the 20 base pair region surrounding the Ume6 motif (SEQ ID NO: 11). Rectangle indicates strongly protected region where Ume6 physically sits, providing base-pair level resolution. In comparison, ChIP-Seq provided diffuse and broad peaks with poor resolution (FIG. 12C).

SEQUENCE LISTING

Figure 1:
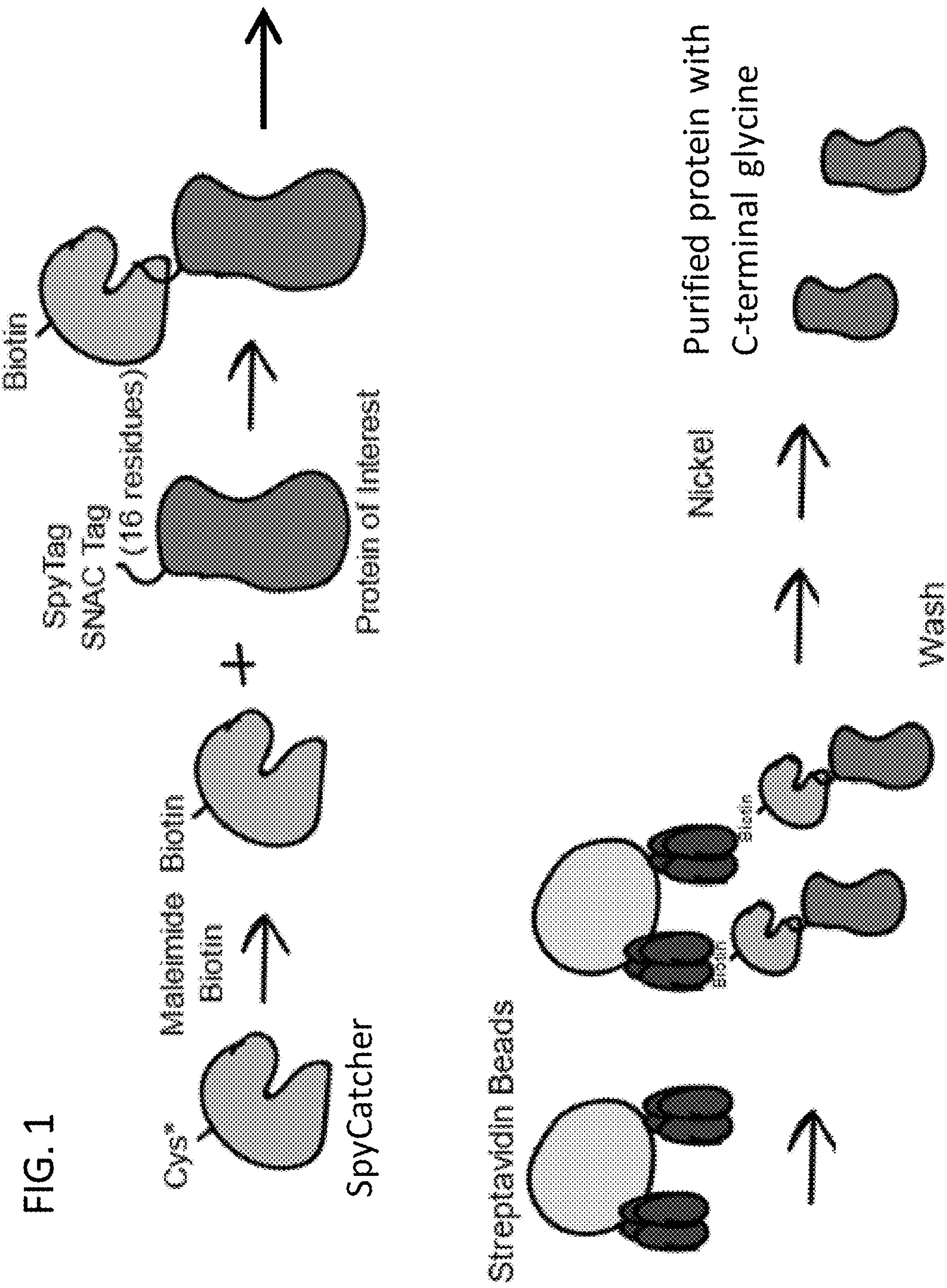
FIG. 1 is a schematic diagram showing an exemplary embodiment of protein purification utilizing a modified SpyCatcher-SpyTag system. The modified SpyCatcher includes a cysteine residue utilized to biotinylate the protein. A protein of interest is tagged with a SpyTag-sequence-specific nickel assisted cleavage (SNAC) Tag. The biotinylated SpyCatcher and SpyTagged protein of interest are contacted under conditions sufficient for the SpyTag to bind to the SpyCatcher. The resulting complex is incubated with streptavidin beads to collect the complex, followed by washing and contacting with nickel, to cleave the SNAC tag and leave purified protein with a single added glycine.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named 1505-102818-03_ST25.txt, which was created on Jan. 31, 2022, and is 18,825 bytes, which is incorporated by reference herein.

SEQ ID NO: 1 is an exemplary SpyTag amino acid sequence.

SEQ ID NO: 2 is an exemplary SpyTag002 amino acid sequence.

SEQ ID NO: 3 is an exemplary SpyTag002 amino acid sequence with linker (9XGGS SpyTag002).

SEQ ID NO: 4 is an exemplary SNAC tag amino acid sequence.

SEQ ID NO: 5 is an exemplary combined SpyTag002/SNAC tag amino acid sequence.

SEQ ID NO: 6 is the amino acid sequence of a SpyCatcher002 protein.

SEQ ID NO: 7 is the amino acid sequence of an exemplary modified SpyCatcher002 protein (S50C).

SEQ ID NO: 8 is the amino acid sequence of an exemplary modified SpyCatcher002 protein (S50C) with 6×His tag (amino acids 5-10) and linker including TEV cleavage site (amino acids 11-25).

SEQ ID NO: 9 is the amino acid sequence of an exemplary MNase-modified SpyCatcher002 protein (S50C) fusion protein with 6×His tag and linker with TEV cleavage site. 6×His Tag: amino acids 3-8; MNase: amino acids 11-159; GGS linker: amino acids 160-174; linker with TEV cleavage site (amino acids 175-190); SpyCatcher002 (S50C): amino acids 191-309.

SEQ ID NO: 10 is a nucleic acid sequence encoding the MNase-modified SpyCatcher002 protein (S50C) fusion protein of SEQ ID NO: 9.

SEQ ID NO: 11 is the nucleic acid sequence of a Ume6 binding motif.

SEQ ID NO: 12 is the nucleic acid sequence of an exemplary vector for expression of a MNase-modified SpyCatcher002 protein (S50C) fusion protein.

SEQ ID NO: 13 is a nucleic acid encoding the modified SpyCatcher002 protein (S50C) of SEQ ID NO: 7.

DETAILED DESCRIPTION

A system to create protein fusions was recently developed, where a small "SpyTag" peptide can rapidly form a spontaneous covalent bond with a~15 kDa "SpyCatcher" domain. While SpyCatcher/SpyTag pairs have become popular for creating proteins with unique topologies (e.g., scaffolds, hydrogels and forced dimerization platforms), their implementation as molecular genetics and biochemical tools has been lacking. Disclosed herein are constructs, systems, and methods to implement a molecular genetics toolkit whereby a single, SpyTagged strain can be combined with a host of standardized, purified reagents or simple plasmid transformations to probe a various molecular processes.

The small size (~13 amino acids) of the SpyTag makes it a noninvasive means of tagging a protein, since there is lower likelihood that a small peptide will disrupt protein folding than a larger and bulkier epitope. The covalent conjugation of SpyCatcher to SpyTag offers an enticing solution to bringing multiple functionalities to a target protein because the single SpyTag can act as a homing signal for many SpyCatcher-fused domains. Because each unit conjugates post-folding, there is a greater capacity to add larger functional domains to a target protein that would typically interrupt native folding in a directly fused context. As disclosed herein, SpyCatcher/SpyTag pairs are a highly promising system to incorporate multiple functionalities into target proteins of interest with the goal of bringing all possible functional domains through a single tag.

While the embodiments described herein utilize SpyCatcher/SpyTag pairs, other peptide-domain pairs capable of forming a covalent peptide bond are also contemplated for the systems and methods provided herein. Exemplary Catcher/Tag pairs include SpyCatcherΔN1ΔC1/SpyTag, SpyLigase/SpyTag or KTag, SnoopTag/SnoopCatcher, SpyCatcher002/SpTag002, SnoopLigase/SnoopTagJr or DogTag, and SpyDock/SpyTag002 (see, e.g., Hatlem et al., *Int. J. Mol. Sci.* 20:2129, 2019).

I. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Heterologous: A nucleic acid or polypeptide that is not naturally occurring or has a sequence that is made by an artificial combination of two otherwise separated segments of nucleotides or amino acids. The term heterologous includes nucleic acids or polypeptides that have been altered solely by addition, substitution, or deletion of a portion of the nucleic acid sequence or amino acid sequence, respectively. In other examples of the use of the term heterologous, a nucleic acid encoding a polypeptide or portion thereof is operably linked to a heterologous nucleic acid encoding a second polypeptide or portion thereof, for example to form a non-naturally occurring fusion protein. This non-naturally occurring nucleic acid or polypeptide is often accomplished by chemical synthesis or, more commonly, by the artificial manipulation of isolated segments of nucleic acids, e.g., by genetic engineering techniques.

Isolated or Purified: An "isolated" or "purified" biological component (such as a nucleic acid, peptide, protein, protein complex, or protein-nucleic acid complex) is one that has been substantially separated, produced apart from, or purified away from other biological components, such as other chromosomal and/or extra-chromosomal DNA and RNA, and proteins. Nucleic acids, peptides, and proteins that have been "isolated" or "purified" thus include nucleic acids and proteins purified by standard purification methods. The term also embraces nucleic acids, peptides, and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is within a cell or other production vessel. Preferably, a preparation is purified such that the biological component represents at least 50%, such as at least 70%, at least 90%, at least 95%, or greater, of the total biological component content of the preparation.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked DNA sequences are contiguous and, where necessary to join two protein-coding regions, in the same reading frame.

SpyCatcher/SpyTag: A system based on an internal isopeptide bond formed in the CnaB2 domain of the *Streptococcus pyogenes* FbaB protein. SpyCatcher is an immunoglobulin-like domain of about 138 amino acids from the CnaB2 domain containing a reactive lysine and catalytic glutamate and SpyTag is a peptide of about 13 amino acids containing a reactive aspartate. SpyCatcher and SpyTag bind with high affinity and spontaneously form a covalent peptide bond (Zakeri et al., *Proc. Natl. Acad. Sci. USA* 109:E690-E697, 2012). In one example, the SpyCatcher protein has the amino acid sequence of GenBank Accession No. AFD50637 (incorporated herein by reference as present in GenBank on Jun. 24, 2020). In one example, the SpyTag peptide has the amino acid sequence AHIVMVDAYKPTK (SEQ ID NO: 1) or VPTIVMVDAYKRYK (SpyTag002; SEQ ID NO: 2).

Transduced or Transformed: A virus or vector "transduces" a cell when it transfers nucleic acid into the cell. A cell is "transformed" by a nucleic acid transduced into the cell when the nucleic acid becomes replicated by the cell, either by incorporation of the nucleic acid into the cellular genome, or by episomal replication. As used herein, the term transformation encompasses all techniques by which a nucleic acid molecule might be introduced into such a cell, including bacterial conjugation, transfection with viral vectors, transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cell. Exemplary vectors include those for use in *E. coli* or *S. cerevisiae*.

II. SpyCatcher/SpyTag Constructs

A. Modified SpyCatcher Constructs

Disclosed herein are modified SpyCatcher polypeptides that can be used in the methods provided. In particular embodiments, the modified SpyCatcher polypeptide includes at least one heterologous (non-naturally occurring) cysteine residue. In embodiments, the modified SpyCatcher protein includes a cysteine at amino acid position 50 (e.g., position 50 of SEQ ID NO: 6), replacing the native serine residue (S50C). In some examples, the modified SpyCatcher protein includes or consists of the amino acid sequence of SEQ ID NO: 7. In other examples, the modified SpyCatcher protein has at least 95% sequence identity (for example, at least 96%, 97%, 98%, 99%, or more identity) with SEQ ID NO: 7, provided that it includes a cysteine at an amino acid position corresponding to amino acid 50 of SEQ ID NO: 7.

The SpyCatcher protein can be modified to introduce a cysteine residue at other positions instead of or in addition to amino acid position 50 (e.g., position 50 of SEQ ID NO: 6). Target amino acids for introduction of a cysteine residue include surface-exposed amino acids in loops of the SpyCatcher protein. Exemplary positions include S24, A25, A41, A43, S51, G52, S56, G84, and G99 of SEQ ID NO: 6. Such sites can be selected and tested by one of ordinary skill in the art.

Also provided are modified SpyCatcher proteins including a tag, such as an affinity tag. In embodiments, the protein is a modified SpyCatcher with a cysteine at amino acid position 50 with a tag (such as biotin) covalently linked to the cysteine. In one non-limiting example, the modified SpyCatcher protein includes the amino acid sequence of SEQ ID NO: 7 with a biotin covalently linked to amino acid 50 (cysteine). The tag is covalently linked to the cysteine either directly (e.g., by a thioester bond) or indirectly (e.g., via a linker). In some examples, the tag (e.g., biotin) is linked to a cysteine residue in the modified SpyCatcher protein utilizing a maleimide or succinimide linker.

In additional embodiments, a modified SpyCatcher protein is covalently linked to a protein of interest (e.g., a functional protein or a protein domain having an activity of interest). In some examples, the modified SpyCatcher protein is covalently linked to the C-terminal end of the protein of interest. In other examples, the modified SpyCatcher protein is covalently linked to the N-terminal end of the protein of interest. In particular examples, the covalent linkage is a peptide bond; however, other covalent linkages, such as thiol or ester bonds are also contemplated. In some examples, the SpyCatcher protein and/or the protein of interest does not include an N-terminal methionine; however, an N-terminal methionine can be present, for example as a result of expression in a bacterial, yeast, or mammalian system. In some examples, the SpyCatcher polypeptide covalently linked to the protein of interest also includes a tag linked to a heterologous cysteine in the SpyCatcher polypeptide.

In particular embodiments, the SpyCatcher protein is covalently linked to a nuclease or a protein domain having nuclease activity. In some embodiments, the nuclease is micrococcal nuclease. In one non-limiting example, the modified SpyCatcher protein covalently linked to a micrococcal nuclease includes or consists of the amino acid sequence of SEQ ID NO: 9. In other examples, the modified SpyCatcher protein has at least 95% sequence identity (for example, at least 96%, 97%, 98%, 99%, or more identity) with SEQ ID NO: 9.

In other examples, the SpyCatcher protein is covalently linked to a catalytically inactive Cas9 protein, such as dCas9. In further examples, the SpyCatcher protein is linked to a protein that can bind to a selected portion of the genome, such as a customized zinc finger domain or TAL effector domain. In a still further example, the SpyCatcher protein is linked to a Tn5 transposase. In each example, the SpyCatcher polypeptide may also include a tag linked to a heterologous cysteine in the SpyCatcher polypeptide.

In some examples, a linker is included between the SpyCatcher polypeptide and the functional protein or domain (such as a nuclease, catalytically inactive Cas9, or transposase). The linker can be a cleavable linker in some examples. In other examples, the linker provides flexibility between the components of the fusion protein. In some examples, the linker is a GGS sequence. In some examples, the linker includes 2 or more repeats of GGS (e.g., 2, 3, 4, 5, 6, 7, 8, or 9 repeats). In other examples, the linker is a cleavable sequence, such as a protease recognition site. In one example, the linker includes a tobacco etch virus (TEV) protease cleavage site.

B. SpyTag Constructs

Also provided are tags that bind to the modified SpyCatcher proteins disclosed herein. In some examples, the tag is a SpyTag (e.g., SEQ ID NO: 1 or SEQ ID NO: 2) or a variant thereof. In other examples, the tag includes one or more additional sequences, such as a sequence-specific nickel assisted cleavage (SNAC) tag (Dang et al., Nature Methods 16:319-322, 2019) and/or an epitope tag (e.g., a FLAG or Myc tag). In some examples, the tags include or consist of SEQ ID NOs: 1-3 (SpyTags), SEQ ID NO: 4 (SNAC tag), and/or SEQ ID NO: 5 (combined Spy-SNAC tag).

Figure 5:
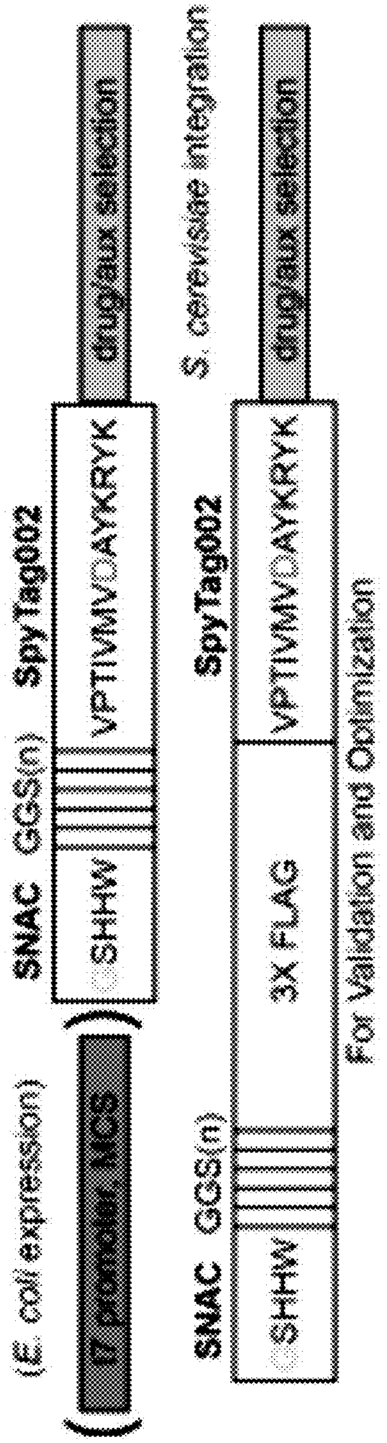
FIG. 5 shows a schematic diagram of an exemplary SpyTag-SNAC tagging vector (top) and an exemplary SpyTag-SNAC validation tagging vector with internal FLAG control tag (bottom). The SNAC tag has the amino acid sequence of SEQ ID NO: 4. The SpyTag002 has the amino acid sequence of SEQ ID NO: 2.

The general features of a cleavable SpyTag-SNAC tag are shown in FIG. 5. In this embodiment a C-terminal SpyTag sequence fused to a protein of interest is used to covalently attach to a SpyCatcher polypeptide. Thus, in some embodiments, the tag includes (from N-terminal to C-terminal), a SNAC tag, a flexible GGS sequence with a length that is varied from 0-9 copies, and a SpyTag (e.g., SpyTag002). Cleavage of the SNAC tag by $Ni^{2+}$ releases everything C-terminal to the glycine of the SNAC tag. For validation, parallel vectors with a 3×FLAG sequence between the SpyTag and SNAC tag are produced.

In an alternative embodiment, an N-terminal SpyTag-SNAC tag fused to a protein of interest is used to covalently attach to a SpyCatcher polypeptide. Thus, in some embodiments, the tag includes (from N-terminal to C-terminal) a SpyTag (e.g., SpyTag002), a flexible GGS sequence with a length that varies from 0-9 copies, and a SNAC tag. In this embodiment, the protein of interest would follow the SNAC tag and cleavage of the SNAC tag occurs after the glycine, and would leave 4 amino acids of the SNAC tag on the protein of interest.

In some examples, the tag is linked to (e.g., operably linked to) a protein of interest or a nucleic acid sequence encoding a protein of interest. The inclusion of a SNAC tag (e.g., SEQ ID NO: 4) in some embodiments provides the ability to cleave the tag off of the protein of interest by addition of $Ni^{2+}$ (e.g., about 1 mM $Ni^{2+}$), leaving only a single glycine residue on the protein of interest. The SNAC tag in some examples, is amino terminal to the SpyTag in the disclosed constructs. In some examples, the protein of interest does not include an N-terminal methionine; however, an N-terminal methionine can be present, for example as a result of expression in a bacterial, yeast, or mammalian system.

In some examples, a linker is included between the tags, and/or between the tag and the protein of interest. The linker can be a cleavable linker in some examples. In other examples, the linker provides flexibility between the components of the fusion protein. In some examples, the linker is a GGS sequence. In some examples, the linker includes one or more repeats of GGS (e.g., 1, 2, 3, 4, 5, 6, 7, 8, or 9 repeats). In other examples, the linker includes a cleavable sequence, such as a protease recognition site. In one example, the linker includes a tobacco etch virus (TEV) protease cleavage site.

The protein of interest is any protein which is of interest for purification, mapping, targeting, or other techniques, including the methods provided herein. In some examples, the protein of interest is a bacterial protein, a yeast protein, or a mammalian protein (such as a mouse, rat, bovine, ovine, porcine, non-human primate, or human protein). Exemplary proteins are described in the Examples; however, the constructs and methods are not limited to these proteins.

C. Nucleic Acids and Vectors

Nucleic acids encoding the modified SpyCatcher polypeptides, SpyCatcher polypeptides linked to a functional protein or domain, and/or SpyTagged and/or SpyTag-SNAC tagged proteins of interest are also provided herein.

In one non-limiting example, a nucleic acid encoding an exemplary MNase-modified SpyCatcher002 protein (S50C) fusion protein includes or consists of SEQ ID NO: 10. In other examples, the nucleic acid encoding an exemplary MNase-modified SpyCatcher002 protein (S50C) fusion protein has at least 95% sequence identity (for example, at least 96%, 97%, 98%, 99%, or more identity) with SEQ ID NO: 10.

Also provided are vectors including nucleic acids encoding the modified SpyCatcher proteins, SpyCatcher proteins linked to a protein of interest (such as a functional protein or domain), and/or SpyTagged proteins of interest. Vectors encoding the disclosed polypeptides may also include regulatory elements such as promoters, enhancers, and 3' regulatory regions, the selection of which will be determined based upon the type of cell in which the protein is to be expressed.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7, and lambda $P_L$ promoters. Methods and plasmid vectors for producing heterologous proteins in bacterial, yeast, or mammalian cells are known to one of ordinary skill in the art.

Suitable prokaryotic cells for expression of the disclosed polypeptides include *Escherichia coli* and *Bacillus subtilis*. In particular examples, the vector is a bacterial expression vector, including but not limited to pETM14 or pDEST14. The disclosed polypeptides can also be expressed in eukaryotic expression systems, including *Pichia pastoris, Drosophila*, Baculovirus, and Sindbis expression systems (e.g., Invitrogen, Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express the polypeptides. Regulatory regions suitable for use in these cells include, for mammalian cells, viral promoters such as those from CMV, adenovirus or SV40, and for yeast cells, the promoter for 3-phosphoglycerate kinase or alcohol dehydrogenase.

In some embodiments, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDRS). In addition, many inducible promoters are of use, such as GAL1-10 (induced by galactose), PHO5 (induced by low extracellular inorganic phosphate), and tandem heat shock HSE elements (induced by temperature elevation to 37 °C). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. In particular examples, the vector includes an ADH1 promoter or a GAL1-10 promoter. In some examples, a low copy expression is selected. A low copy vector may be particularly useful for embodiments using dCas9 targeting, to have limiting amounts of SpyCatcher-dCas9 or dCas9-SpyCatcher fusion protein present to avoid saturating target binding sites.

In one non-limiting example, a vector encoding an MNase-modified SpyCatcher002 protein (S50C) fusion protein has at least 95% sequence identity (for example, at least 96%, 97%, 98%, 99%, or more identity) to the nucleic acid sequence of SEQ ID NO: 12. In particular examples, the vector includes or consists of the nucleic acid sequence of SEQ ID NO: 12.

III. Methods of Protein Purification

One of the most fundamental strategies to study protein function is to purify a protein of interest to homogeneity and assay its activity on known or suspected substrates. This basic biochemical strategy has been employed to determine structure-function relationships for proteins involved in nearly all life processes. A common strategy to purify a protein from source (e.g., from *S. cerevisiae*) is to append the protein with an epitope tag and isolate the protein from cellular lysate by capturing the epitope via affinity purification. In yeast, one of the most widely used epitopes for this purpose is the addition of a "FLAG" tag. FLAG-containing proteins are then harvested from source using anti-FLAG antibodies conjugated to agarose affinity gel or magnetic beads, then released by competing with excess FLAG peptide.

There are several drawbacks to this approach that, if corrected, would greatly improve protein purification methods. First, the incorporation of an antibody epitope can disrupt protein folding or function. In addition, the binding of an epitope to antibodies is relatively slow ($k_a$~$10^3M^{-1}s^{-1}$) and requires long incubation with crude lysate for efficient protein binding, which can lead to proteolysis and loss of functional protein. The low (near micromolar) affinity of epitope/antibody (e.g., FLAG/anti-FLAG) makes it difficult to quickly and fully capture a protein of interest. Protein elution is performed by competition with excess epitope peptide, leading to contamination of the final purified product with a confounding factor. In addition, antibodies utilized in these methods can be cross-reactive with proteins from yeast to mammals. Finally, both epitope peptide and anti-epitope resin are expensive.

In some embodiments, the disclosed methods use SpyCatcher/SpyTag pairs to purify proteins from source without the need for antibodies. In some examples, the method utilizes a purified SpyCatcher domain containing a reactive cysteine that is tagged (e.g., with biotin). A peptide that binds to the SpyCatcher domain (e.g., a SpyTag peptide or a SpyTag-SNAC tag peptide) is added to a protein of interest, similar to tagging with an epitope, such as FLAG. The tagged SpyCatcher is incubated with a mixture (such as a cell lysate) containing a SpyTagged protein of interest, under conditions sufficient for the SpyTag to bind to (e.g., covalently link) the SpyCatcher of the target protein. After incubation with a binding partner (e.g., streptavidin resin or streptavidin beads), the protein of interest can be washed and eluted by cleaving the tag (for example by addition of 1 mM $Ni^{2+}$) to leave behind the purified protein of interest with a single additional glycine from the cleaved SNAC tag. In embodiments that do not include the SNAC tag (e.g., only the SpyTag), the protein is released using high salt conditions.

An exemplary embodiment is shown in FIG. 1. In some embodiments, the methods includes contacting a modified SpyCatcher polypeptide linked to a tag (such as biotin) with a protein of interest covalently linked to a SpyTag polypeptide or a SpyTag-SNAC tag polypeptide under conditions sufficient for the SpyCatcher polypeptide and the SpyTag polypeptide or SpyTag-SNAC tag polypeptide form a covalently bound SpyCatcher-SpyTag-protein complex or a SpyCatcher-SpyTag-SNAC tag-protein complex and contacting the SpyCatcher-SpyTag-protein complex or SpyCatcher-SpyTag-SNAC tag-protein complex with a binding partner for the tag covalently linked to the SpyCatcher polypeptide (e.g., streptavidin) under conditions sufficient for the binding partner to bind to the tag. The complex is then washed, for example to remove unbound protein and the SpyTag or the SpyTag-SNAC tag is cleaved from the complex, followed by recovery and/or analysis of the purified protein.

In some examples, the methods include contacting a SpyCatcher polypeptide including a tag covalently linked to a heterologous cysteine residue with a protein of interest covalently linked to a SpyTag polypeptide or a SpyTag-SNAC tag polypeptide, under conditions sufficient for the SpyCatcher polypeptide and the SpyTag polypeptide or SpyTag-SNAC tag polypeptide to form a covalently bound SpyCatcher-SpyTag-protein of interest complex or a SpyCatcher-SpyTag-SNAC tag-protein of interest complex, and contacting the SpyCatcher-SpyTag-protein of interest complex or SpyCatcher-SpyTag-SNAC tag-protein of interest complex with a binding partner for the tag covalently linked to the SpyCatcher polypeptide under conditions sufficient for the binding partner to bind to the tag. The complex is washed one or more times, the SpyTag or SpyTag-SNAC tag is cleaved from the complex, and the protein of interest is isolated. In some examples, contacting the SpyCatcher polypeptide with the protein of interest covalently linked to the SpyTag polypeptide or the SpyTag-SNAC tag polypeptide is performed in a lysate of a cell expressing the protein of interest covalently linked to the SpyTag polypeptide or the SpyTag-SNAC tag polypeptide. In one non-limiting example, the tag on the modified SpyCatcher polypeptide is biotin, and the binding partner for the tag is streptavidin.

In some non-limiting embodiments, the methods are carried out in vitro. In one example, a cell expressing the SpyTagged protein of interest is lysed. The cell lysate is incubated with tagged (e.g., biotinylated) SpyCatcher for about 30 minutes to 4 hours (e.g., about 1-3 hours) at 4 °C. The tag binding partner (e.g., streptavidin, such as streptavidin resin or streptavidin beads) is added, for example for about 10-60 minutes (e.g., about 10-20 minutes) at about 4 °C. The complex is then washed, at a stringency level selected depending on the protein being purified and/or downstream use. For example, for a purified enzyme or for analyzing associated proteins (e.g., by mass spectrometry), a moderately stringent wash is used. For determining modification state of the purified protein, a highly stringent wash is used. Following the washes, the tag is cleaved. In examples using a SNAC tag, cleavage is carried out using nickel (e.g., 1 mM $Ni^{2+}$) for about 1 hour to overnight (e.g., about 1-4 hours, about 2-8 hours, about 6-12 hours, or about 10-18 hours). The purified protein can be collected from the soluble fraction, as it will be dissociated from the tag partner (e.g., streptavidin resin).

In some examples, the protein of interest is tagged with a SpyTag peptide having the amino acid sequence of SEQ ID NO: 1 or SEQ ID NO: 2. In other examples the protein of interest is tagged with a SpyTag-SNAC peptide having the amino acid sequence of SEQ ID NO: 5. The SpyTag-SNAC peptide can be incorporated at the N-terminus, C-terminus or within protein loops, making it a versatile strategy for protein tagging. SpyCatcher-SpyTag pairing occurs quantitatively within about 10-15 minutes of incubation, making biotin-functionalization of the protein of interest rapid. Association kinetics of biotin with streptavidin are thought to be diffusion-limited, and binding affinity is in the femtomolar range, meaning this approach will more rapidly and quantitatively purify the protein of interest. The extremely high affinity allows for robust protein washing and rapid depletion of protein from lysate, leading to purer, less degraded protein. Finally, $Ni^{2+}$ induced cleavage of the SNAC tag is "gentle" and inexpensive.

IV. Methods of Mapping Protein-Nucleic Acid Binding

Determining the genomic locations where proteins interact of nucleic acids in the nucleus is of fundamental importance to molecular biology. The most commonly employed strategy to determine global protein binding sites is to use formaldehyde-assisted chromatin immunoprecipitation, better known as "ChIP." This process uses formaldehyde to fix global protein-DNA contacts in place, then DNA is sheared by sonication and the protein of interest is purified using antibodies to an epitope tag or to the endogenous protein. Protein is removed and resulting DNA footprints are purified, allowing for identification of DNA regions that were co-purified with the protein of interest.

ChIP generally suffers from similar drawbacks to protein purification strategies that use antibodies. First, tagging of proteins with the most common epitopes (e.g., FLAG and Myc) can interfere with protein function or folding. Formaldehyde crosslinking can lead to epitope masking, preventing association of antibody with the desired protein epitope, or protein aggregation leading to identification of false positive associations. Sonication of DNA leads to variable fragment sizes with fragmentation biases for certain genomic regions and low resolution. Further, antibodies suffer from lot-to-lot variability, limited shelf life, relatively low affinity for substrate, promiscuous and/or biased binding to chromatin, and are expensive. Newer high-resolution protein-DNA mapping strategies have been recently developed that avoid crosslinking and/or sonication (e.g., ORGANIC and CUT&RUN), and a single high-resolution antibody-free method (e.g., ChEC-seq) has been developed to map protein-DNA interactions. ChEC-seq requires a bulky C- or N-terminal tag that is anecdotally incompatible with many protein complexes and relies on a combination of nonspecific and specific nuclease cleavage of DNA for fragmentation, making it difficult to validate identified protein-DNA binding sites. CUT&RUN and ORGANIC are both constrained by the limitations imposed by antibodies and have fairly long and complicated workflows.

The SpyCatcher/SpyTag system is utilized herein to develop a versatile, high-resolution and antibody-free strategy to map protein binding sites across the genome. In one embodiment, the methods use biotinylated SpyCatcher to associate with a genome-bound, SpyTagged protein of interest, which is then isolated in complex with DNA binding sites from nuclease-treated, and optionally crosslinked chromatin, and purified with streptavidin beads. This provides a simple workflow that circumvents antibody use and allows for extremely robust washing of protein-DNA complexes before heat-based elution of associated DNA fragments.

A. SpyCatcher-SpyTag Methods with Nuclease

Figure 2:
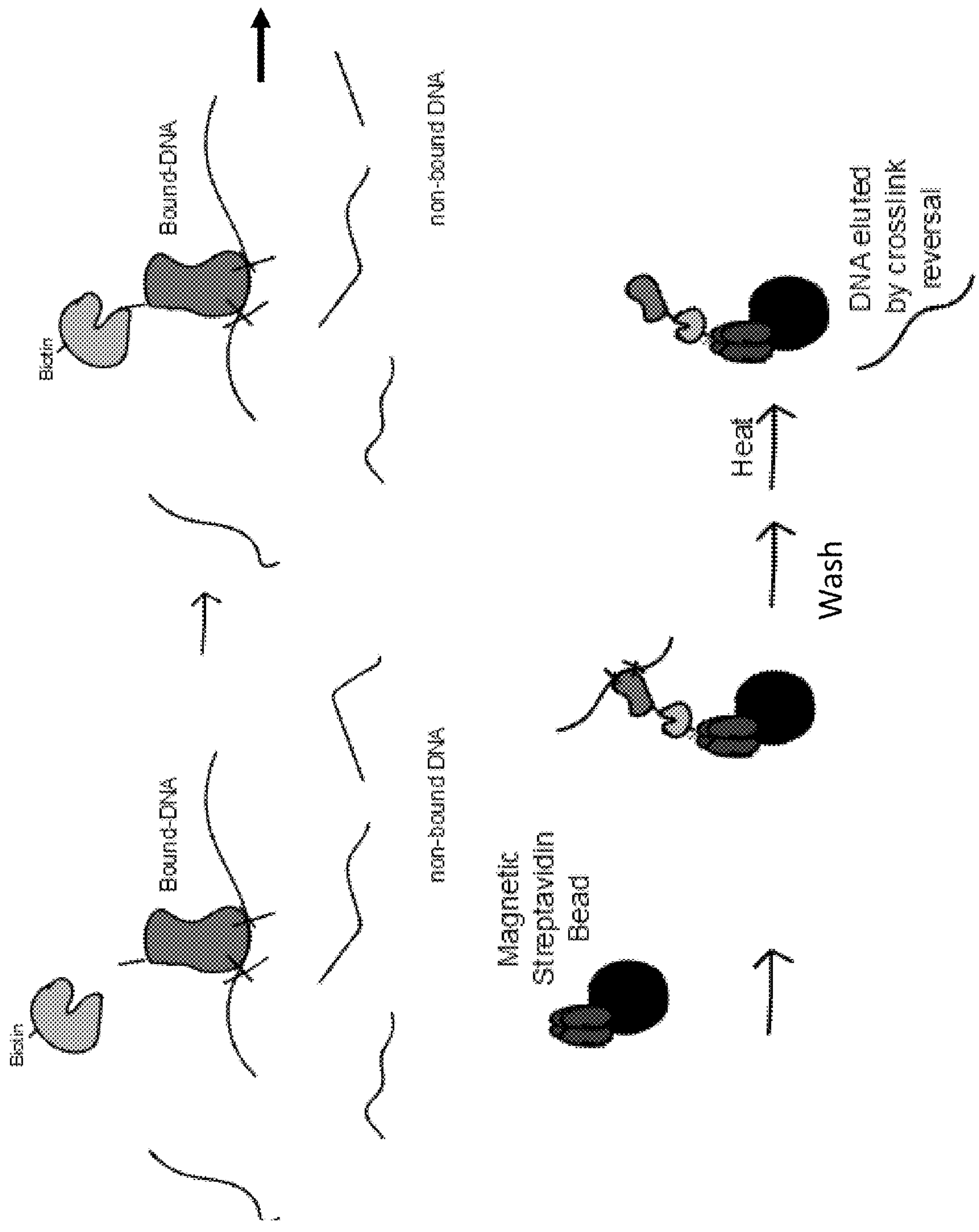
FIG. 2 is a schematic diagram showing an exemplary embodiment of mapping protein binding to nucleic acids using a modified SpyCatcher-SpyTag system. The modified SpyCatcher includes a cysteine residue utilized to biotinylate the protein. A protein of interest is tagged with a SpyTag and is allowed to bind to nucleic acids. The biotinylated SpyCatcher and SpyTagged protein of interest are contacted under conditions sufficient for the SpyTag to bind to the SpyCatcher and then the nucleic acids are cleaved with a nuclease. The resulting complex is incubated with streptavidin beads to collect a complex including the protein of interest and bound nucleic acids. The complex is washed to remove non-bound nucleic acids and the protein complex is eluted from the nucleic acid. The nucleic acid can then be analyzed and identified.

In some embodiments (e.g., illustrated in FIG. 2), the method includes contacting a modified SpyCatcher polypeptide linked to a tag (such as biotin) with a protein of interest covalently linked to a SpyTag polypeptide or a SpyTag-SNAC tag polypeptide and a population of nucleic acids under conditions sufficient for the protein of interest to bind to the nucleic acid and for SpyCatcher polypeptide to bind to the SpyTag polypeptide or SpyTag-SNAC tag polypeptide, forming a SpyCatcher-SpyTag-protein-nucleic acid complex or a SpyCatcher-SpyTag-SNAC tag-protein-nucleic acid complex. The SpyCatcher-SpyTag-protein-nucleic acid complex or SpyCatcher-SpyTag-SNAC tag-protein-nucleic acid complex is contacted with a binding partner for the tag covalently linked to the SpyCatcher polypeptide (e.g., streptavidin) under conditions sufficient for the binding partner to bind to the tag. One or more washes of the complex is performed, for example to remove unbound nucleic acids and/or proteins. The SpyCatcher-SpyTag or SpyCatcher-SpyTag-SNAC tag protein complex is disassociated from the nucleic acid and optionally, the tag is cleaved (e.g., with nickel for a SNAC tag) and the nucleic acid is isolated and/or identified (e.g., by sequencing, PCR, qPCR, or Southern blotting).

In some examples, the methods include contacting a modified SpyCatcher polypeptide including a tag covalently linked to a heterologous cysteine residue with a protein of interest covalently linked to a SpyTag polypeptide or a SpyTag-SNAC tag polypeptide and a population of nucleic acids under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex and contacting the SpyCatcher-SpyTag-protein-nucleic acid complex or SpyCatcher-SpyTag-SNAC tag-protein-nucleic acid complex with a binding partner for the tag covalently linked to the SpyCatcher polypeptide under conditions sufficient for the binding partner to bind to the tag. The complex is contacted with a nuclease under conditions sufficient for the nuclease to cleave the nucleic acid flanking the complex and the complex is washed one or more times. The SpyCatcher-SpyTag-protein or SpyCatcher-SpyTag-SNAC tag-protein is dissociated from the nucleic acid; and the nucleic acid is isolated. In some examples, contacting the modified SpyCatcher polypeptide with the protein of interest covalently linked to the SpyTag polypeptide or the SpyTag-SNAC tag polypeptide and the population of nucleic acids is performed in a permeabilized cell expressing the protein of interest covalently linked to the SpyTag polypeptide or the SpyTag-SNAC tag polypeptide. In one non-limiting example, the tag on the modified SpyCatcher polypeptide is biotin, and the binding partner for the tag is streptavidin. In some examples, the methods further include identifying the isolated nucleic acid.

In one embodiment, the methods include permeabilizing cells expressing a SpyTagged protein of interest. In the case of yeast cells, the cell walls are permeabilized and cells walls are lysed (e.g., using zymolase) in a permeabilization buffer. Alternatively, yeast cells can be mechanically disrupted, for example, using a bead beater, freezer mill, and/or mortar-pestle plus liquid nitrogen. For cells without a cell wall (e.g., mammalian cells), the permeabilization buffer does not include zymolase. In one non-limiting example, the permeabilization buffer is 1 M sorbitol, 50 mM NaCl, 10 mM Tris pH 7.5, 5 mM $MgCl_2$, 0.075% (v/v) TRITON™ surfactant or NP-40, 0.5 mM spermidine and 1 mM beta-Mercaptoethanol. This step may be performed in the presence of tagged (e.g., biotinylated) SpyCatcher, or the tagged SpyCatcher may be added following permeabilization. In some examples, the tagged SpyCatcher is incubated with the permeabilized cells for about 10 minutes to 2 hours (e.g., about 15-30 minutes, about 30-60 minutes, or about 1-2 hours) at about 4 °C. Unconjugated SpyCatcher is removed by washing in the permeabilization buffer and the resulting pellet is resuspended in permeabilization buffer. In some examples, the method optionally includes a cross-linking step (e.g., with 1% formaldehyde for about 15 minutes), followed by quenching with 125 mM glycine. This step can be performed in permeabilized cells or cell lysate.

A nuclease (e.g., micrococcal nuclease is added) and if required, calcium (e.g., 1 mM $CaCl_2$) is added and the mixture is incubated at about 37 °C for about 5-30 minutes (e.g., about 5-15, about 10-20, or about 15-30 minutes). The reaction is quenched, e.g., by addition of EGTA. The complex is collected with streptavidin (e.g., streptavidin resin or streptavidin beads) by incubating for about 10-30 minutes at room temperature. The complex is washed with permeabilization buffer and nucleic acids are released, for example by addition of 1% SDS and heating (e.g., about 5-20 minutes at about 65 °C). The nucleic acids are collected from the supernatant and washed. If crosslinking was used, the washes can include high salt and/or high ionic detergent and an increase in the elution time with SDS (e.g., about 30 minutes to 1 hour). The nucleic acids can be identified (e.g., by sequencing, PCR, qPCR, or Southern blotting).

B. SpyCatcher-Nuclease Fusion Protein Methods

Figure 3:
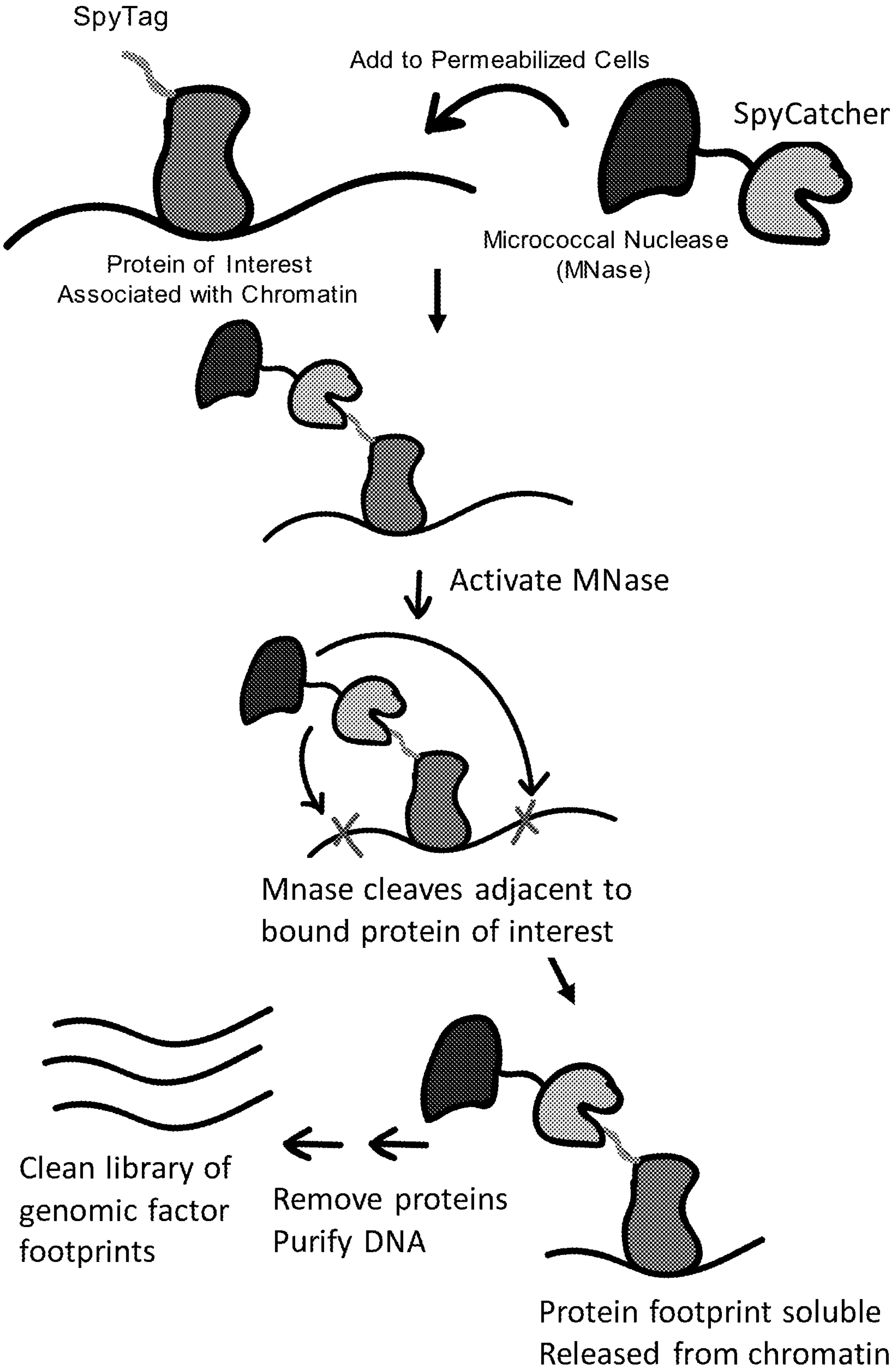
FIG. 3 is a schematic diagram showing a further exemplary embodiment of mapping protein binding to nucleic acids utilizing a modified SpyCatcher-SpyTag system including a nuclease (e.g., micrococcal nuclease) covalently linked to a SpyCatcher protein. A protein of interest is tagged with a SpyTag and is allowed to bind to nucleic acids (e.g., chromatin in a cell). The SpyCatcher-nuclease and SpyTagged protein of interest are contacted under conditions sufficient for the SpyTag to bind to the SpyCatcher. The nuclease is activated, resulting in cleavage of the nucleic acid adjacent to the bound protein of interest. The complex is washed to remove non-bound nucleic acids and the proteins are eluted from the nucleic acid(s). The nucleic acid(s) can then be analyzed and identified.

In some embodiments (see e.g., FIG. 3), the methods include contacting a modified SpyCatcher polypeptide linked to a nuclease (such as micrococcal nuclease) with a protein of interest covalently linked to a SpyTag polypeptide or a SpyTag-SNAC tag polypeptide and a population of nucleic acids under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex. The complex is incubated under conditions sufficient to activate the nuclease (such as in the presence of calcium). One or more washes of the complex is performed, for example to remove unbound nucleic acids and/or proteins. The SpyCatcher-SpyTag or SpyCatcher-SpyTag-SNAC tag is disassociated from the nucleic acid and the nucleic acid is isolated and/or identified (e.g., by sequencing).

In some examples, the methods include associating a SpyTagged protein of interest with DNA, and permeabilized cells are treated with SpyCatcher fused to a nuclease (e.g., micrococcal nuclease). The nuclease is activated to cleave the nucleic acid on either side of the bound protein of interest, thereby solubilizing the DNA footprint where the protein of interest binds. These soluble fragments are isolated from cell lysate and purified away from associated protein and RNA.

In some embodiments, the methods include contacting a SpyCatcher polypeptide covalently linked to a micrococcal nuclease with a protein of interest covalently linked to a SpyTag polypeptide or a SpyTag-SNAC tag polypeptide and a population of nucleic acids, under conditions sufficient for the protein of interest to bind to the nucleic acids and the SpyCatcher polypeptide and the SpyTag polypeptide or SpyTag-SNAC tag polypeptide to bind to form a SpyCatcher-SpyTag-protein-nucleic acid complex or a SpyCatcher-SpyTag-SNAC tag-protein-nucleic acid complex and incubating the SpyCatcher-SpyTag-protein-nucleic acid complex or the SpyCatcher-SpyTag-SNAC tag-protein-nucleic acid complex under conditions sufficient to activate the micrococcal nuclease. The complex is washed one or more times, the SpyCatcher-SpyTag or SpyCatcher-SpyTag-SNAC tag is dissociated from the nucleic acid, and the nucleic acid is isolated. In some examples, contacting the SpyCatcher polypeptide with the protein of interest covalently linked to the SpyTag polypeptide or the SpyTag-SNAC tag polypeptide is performed in a permeabilized cell expressing the protein of interest covalently linked to the SpyTag polypeptide or the SpyTag-SNAC tag polypeptide or in a permeabilized cell co-expressing the SpyCatcher polypeptide and the protein of interest covalently linked to the SpyTag polypeptide or the SpyTag-SNAC tag polypeptide. In some examples, the method also includes identifying the isolated nucleic acid. In additional examples, the SpyCatcher polypeptide covalently linked to the micrococcal nuclease also includes a tag linked to a heterologous cysteine in the SpyCatcher polypeptide.

In some non-limiting embodiments, cells expressing a SpyTagged protein of interest are permeabilized (and cell walls are lysed, if applicable, by inclusion of zymolase) in permeabilization buffer. In one non-limiting example, the permeabilization buffer is 1 M sorbitol, 50 mM NaCl, 10 mM Tris pH 7.5, 5 mM $MgCl_2$, 0.075% (v/v) TRITON™ surfactant or NP-40, 0.5 mM spermidine and 1 mM beta-Mercaptoethanol. This step may be performed in the presence of SpyCatcher-nuclease fusion protein, or the SpyCatcher-nuclease fusion protein may be added following permeabilization. In some examples, the SpyCatcher-nuclease is incubated with the permeabilized cells for about 10 minutes to 2 hours (e.g., about 15-30 minutes, about 30-60 minutes, or about 1-2 hours) at about 4 °C. Unconjugated SpyCatcher is removed by washing in the permeabilization buffer and the resulting pellet is resuspended in permeabilization buffer. The nuclease is activated, for example with $CaCl_2$ (about 1 mM) for about 15 seconds to 1 minute for micrococcal nuclease and rapidly quenched with excess EGTA. DNA is recovered, for example, by centrifugation and collecting supernatant, which contains fragmented DNA that was adjacent to protein of interest. Alternatively, all DNA is purified by phenol/chloroform extraction and ethanol precipitation and small fragments are selected for analysis (e.g., high throughput sequencing, PCR methods, etc.). The resulting method is a faster, cheaper, crosslinking-free and antibody-free way to achieve high-resolution binding profiles comparable to cutting-edge protein mapping strategies. If chromatin is crosslinked and the MNase-SpyCatcher reagent is biotinylated, very stringent washes can be added to allow for extremely low background, antibody-free and high-resolution protein mapping.

In a still further embodiment, both the SpyTagged protein of interest and the SpyCatcher-nuclease fusion protein are co-expressed in the same cell. The cell can be in vitro. In this example, the method includes permeabilizing the cell and activation of the nuclease (for example, as described above). In another example, the cells expressing the SpyTagged protein of interest and the SpyCatcher-nuclease fusion may be in vivo. In this example, the SpyTagged protein of interest can be expressed generally (for example, in many or all cells in an organism) and the SpyCatcher-nuclease is expressed in a cell population of interest (e.g., a particular cell type or organ). The cells co-expressing the two constructs can be isolated and are then analyzed as described above.

Association of SpyCatcher with SpyTag is significantly faster than association of antibody with an epitope tag. Thus, the disclosed strategies provide flexibility in protein mapping methods, allowing for rapid, lower-resolution antibody-free binding site identification with biotin-SpyCatcher or ultra-high resolution, noise-free mapping with biotinylated MNase-SpyCatcher. The method allows for a ChEC-seq analog, where MNase-SpyCatcher is induced in a strain with a SpyTagged protein of interest and solubilization of protein-bound DNA fragments is driven by $Ca^{2+}$ treatment. In sum, a single SpyTag on a target protein can be used to map protein binding sites through multiple strategies that do not require expensive antibodies or bulky epitope tags. This cheaper, faster method to identify binding sites will be a significant upgrade to current mapping methods and will lead to easier analysis of protein function.

In some examples, Reb1, Abf1, Rap1, or Ume6 are tagged with a C-terminal SpyTag (and optionally also a FLAG tag for initial validation). These factors are chosen because they have been used extensively as standard DNA binding factors for protein mapping studies in yeast. Cultures are grown to mid-log stage and split in two for downstream processing. Half are crosslinked, permeabilized, incubated with antibody, incubated with secondary antibody, treated with calcium and soluble fragments are be collected for sequencing library preparation (CUT&RUN strategy). The second half is permeabilized, treated briefly with purified MNase-SpyCatcher, treated with calcium, and soluble DNA fragments are collected for sequencing. The treatment for CUT&RUN consists of roughly 6 hours of incubations and washes whereas the treatment for the disclosed method is ~30 minutes or less. Protein binding sites are identified from sequenced libraries and compared to each other and all previous protein mapping methods.

C. Additional Methods

Tn5 transposase integrates adapters in the proximity of the bound protein that can be used to determine the genomic location of the bound protein. Though not cleaving the site of interest, it leaves a "mark" that can readily be detected via methods such as high throughput sequencing (see, e.g., Kaya-Okur et al., *Nat. Commun.* 10:390, 2019). In some embodiments, the methods include contacting a SpyCatcher polypeptide linked to Tn5 transposase with a protein of interest covalently linked to a SpyTag polypeptide or a SpyTag-SNAC tag polypeptide and a population of nucleic acids under conditions sufficient for the protein of interest to bind to the nucleic acids and the SpyCatcher-Tn5 polypeptide and the SpyTag polypeptide or SpyTag-SNAC tag polypeptide to bind to form a SpyCatcher-Tn5-SpyTag-polypeptide-nucleic acid complex or a SpyCatcher-Tn5-SpyTag-SNAC tag-polypeptide-nucleic acid complex. In some examples, the SpyCatcher polypeptide linked to Tn5 transposase and the protein of interest covalently linked to a SpyTag polypeptide or a SpyTag-SNAC tag polypeptide are coexpressed in a cell. The complex is incubated under conditions sufficient to activate the transposase (such as addition of $Mg^{2+}$). One or more washes of the complex is performed, for example to remove unbound nucleic acids and/or proteins. The SpyCatcher-SpyTag or SpyCatcher-SpyTag-SNAC tag is disassociated from the nucleic acid and the nucleic acid is isolated and/or identified (e.g., by sequencing).

V. Methods to Localize Proteins to Desired Nucleic Acid Locations

Researchers often wish to know the function of chromatin proteins in the context of the nucleus. To determine protein function at genomic targets, scientists have developed engineered strategies to recruit proteins to ectopic regions and investigate effects on local DNA-dependent processes. Historically, fusions of sequence-specific DNA binding domains to proteins of interest (e.g., LexA fusions) were used to bring proteins to LexA binding sites, which need to be inserted ectopically at genomic regions. While this method is still employed today, cutting-edge methods use fusions of TAL-Effector DNA binding domains or catalytically inactive dCas9 to recruit proteins to pre-existing binding sites to determine their function in vivo. All of these strategies suffer from the limitation that the protein fusions are considerably large and render many proteins of interest non-functional (e.g., dCas9 is ~165 kDa), and are difficult to design, clone and create.

Figure 4:
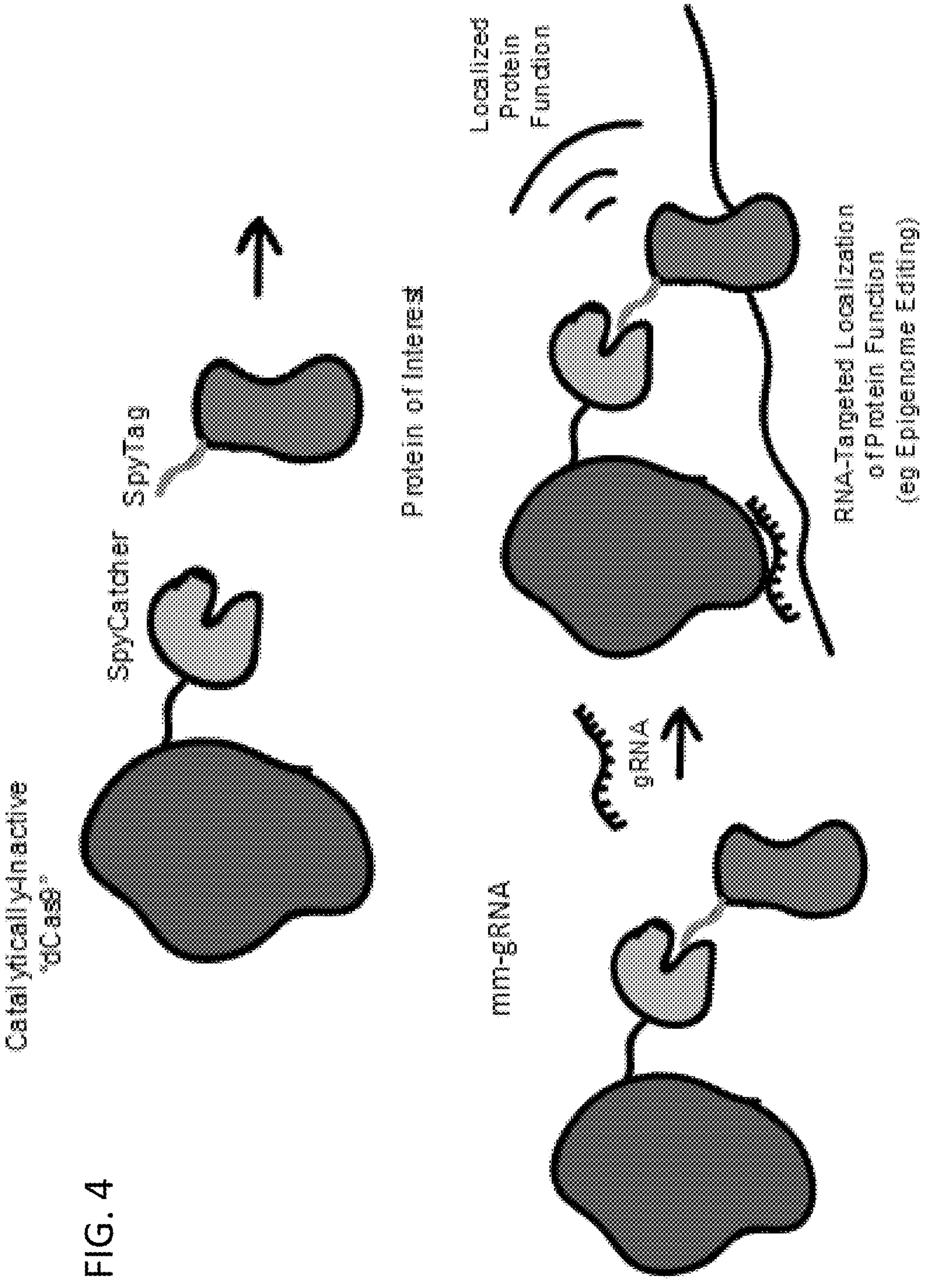
FIG. 4 is a schematic diagram showing an exemplary embodiment of nucleic acid targeting utilizing a modified SpyCatcher-SpyTag system including a dCas9 nuclease covalently linked to a SpyCatcher protein and a guide RNA. A protein of interest is tagged with a SpyTag and the SpyCatcher and SpyTagged protein of interest are contacted under conditions sufficient for the SpyTag to bind to the SpyCatcher. The complex is contacted with nucleic acids in the presence of a guide RNA (gRNA) that targets the complex to a nucleic acid of interest via the dCas9. The protein of interest may be a functional protein or domain thereof with activity at the nucleic acid of interest (e.g., epigenomic editing).

Disclosed herein is a simple approach to bring any protein of interest to any genomic location through a versatile and modular design. The method uses catalytically inactive dCas9 fused to SpyCatcher to convert a SpyTagged protein to a targetable moiety within the nucleus. By adding a short SpyTag to a protein under investigation, dCas9-SpyCatcher can be introduced by plasmid transformation and guide RNAs can be added to localize the desired protein to a targeted genomic location (e.g., FIG. 4). Protein function can then be assessed by determining local changes in transcription, chromatin state or other suspected processes at the targeted region. Multiple genomic contexts can be investigated by swapping gRNAs, and alternate proteins can be tested by switching which protein is SpyTagged. Single genomic contexts can be simultaneously targeted by multiple proteins by appending SpyTag on multiple proteins in the same cell for multiplexed modification of a genomic locus.

In some embodiments, the method includes contacting a modified SpyCatcher polypeptide linked to an inactive Cas9 (e.g., dCas9) with a protein of interest covalently linked to a SpyTag polypeptide or a SpyTag-SNAC tag polypeptide, a guide RNA, and a population of nucleic acids under conditions sufficient for the SpyCatcher polypeptide and the SpyTag polypeptide or SpyTag-SNAC tag polypeptide and nucleic acids to form a SpyCatcher-SpyTag-protein-gRNA-nucleic acid complex or a SpyCatcher-SpyTag-SNAC tag-protein-gRNA-nucleic acid complex. In alternative embodiments, instead of a dCa9 fusion and gRNA for targeting, the SpyCatcher protein is linked to a protein that can bind to a selected portion of the genome, such as a customized zinc finger domain or TAL effector domain.

In some embodiments, the methods include contacting a SpyCatcher polypeptide covalently linked to a dCas9 nuclease with a protein of interest covalently linked to a SpyTag polypeptide or a SpyTag-SNAC tag polypeptide, a guide RNA specific for a target nucleic acid, and a population of nucleic acids under conditions sufficient for the SpyCatcher polypeptide and the SpyTag polypeptide or SpyTag-SNAC tag polypeptide and nucleic acids to form a SpyCatcher-SpyTag-protein-gRNA-nucleic acid complex or a SpyCatcher-SpyTag-SNAC tag-protein-gRNA-nucleic acid complex. In some examples, the methods also include analyzing the target nucleic acid. In additional examples, the SpyCatcher polypeptide covalently linked to the dCas9 also includes a tag linked to a heterologous cysteine in the SpyCatcher polypeptide.

In some non-limiting examples, the components (e.g., SpyTagged protein of interest, SpyCatcher-dCas9 fusion protein, and gRNA) are all co-expressed in a cell. Conjugation of the components occurs spontaneously, and no washes or purifications are needed. The complex will form and the target sequence is modified based on the protein of interest that is brought to the target sequence. Analysis of the target sequence can include RNA purification, chromatin purification, and/or nucleosome mapping, and can be carried out by one of ordinary skill in the art based on the protein of interest and the expected function.

This method provides simplified versatility, enabling any researcher to localize a protein of interest to a specific site using plasmid transformations. While the final fusion proteins are still large (dCas9-Protein), the two components fold separately and are post-translationally fused through a small and flexible SpyTag-SpyCatcher linkage. These attributes minimize loss of function in the context of the fusion protein.

VI. Kits

Provided herein are kits including one or more SpyCatcher polypeptides, nucleic acids, or vectors disclosed herein, which may be used in the provided methods. In some embodiments, the kit includes a modified SpyCatcher protein provided herein (e.g., SEQ ID NO: 7), or a biotinylated SpyCatcher protein. In other embodiments, the kit includes a SpyCatcher-MNase fusion protein (e.g., SEQ ID NO: 9) or a biotinylated SpyCatcher-MNase fusion protein. In further embodiments, the kit includes a SpyCatcher-Tn5 fusion protein or a biotinylated SpyCatcher-Tn5 fusion protein.

In other embodiments, the kit includes a nucleic acid encoding a modified SpyCatcher protein (e.g., a nucleic acid encoding SEQ ID NO: 7). In other embodiments, the kit includes a nucleic acid encoding a SpyCatcher-MNase fusion protein (e.g., a nucleic acid encoding SEQ ID NO: 9). In additional embodiments, the kit further includes a nucleic acid encoding a SpyTag-SNAC tag (e.g., a nucleic acid encoding SEQ ID NO: 5). In any example, the nucleic acid may be included in a vector, for insertion of a nucleic acid encoding a protein of interest.

In some examples, the kits further include one or more containers including some or all of the reagents (such as buffers, nickel, calcium, wash solutions) for carrying out the methods described herein. In additional examples, instructions for use are also included.

EXAMPLES

The following examples are provided to illustrate certain particular features and/or embodiments. These examples should not be construed to limit the disclosure to the particular features or embodiments described.

Example 1

Preparation of Biotinylated SpyCatcher Protein and SpyTagged Constructs

The first step in pulling down SpyTagged proteins using SpyCatcher is purifying and biotinylating a SpyCatcher domain. SpyCatcher002 with a cysteine mutation at position 50 (S50C) has been prepared (SEQ ID NO: 7). This amino acid position is predicted to be reactive based on its surface exposure. This construct was cloned into pDEST14 for IPTG-driven overexpression in *E. coli* and rapid nickel-affinity purification. This construct exhibited robust expression (>50 mg/L culture) and has been purified to homogeneity using nickel affinity (TALON) and anion exchange (QFF) chromatography. After purification, SpyCatcher was incubated with maleimide-biotin at room temperature to conjugate biotin to the reactive cysteine (550C of SEQ ID NO: 7). Unreacted maleimide-biotin was quenched with DTT and removed by desalting. Rapid biotinylation of SpyCatcher (S50C) has been demonstrated, which quantitatively interacts with free streptavidin protein.

Example 2

MNase-SpyCatcher Mapping of Chromatin Binding Sites

Figure 6:
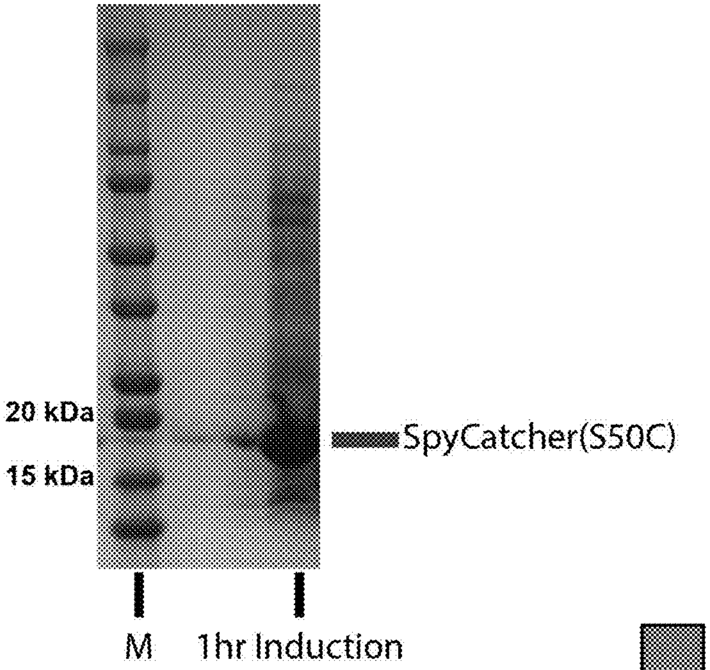
FIG. 6 shows expression of SpyCatcher002 (S50C) after 1 hour induction in *E. coli*. M=BioRad MW marker.
Figure 7:
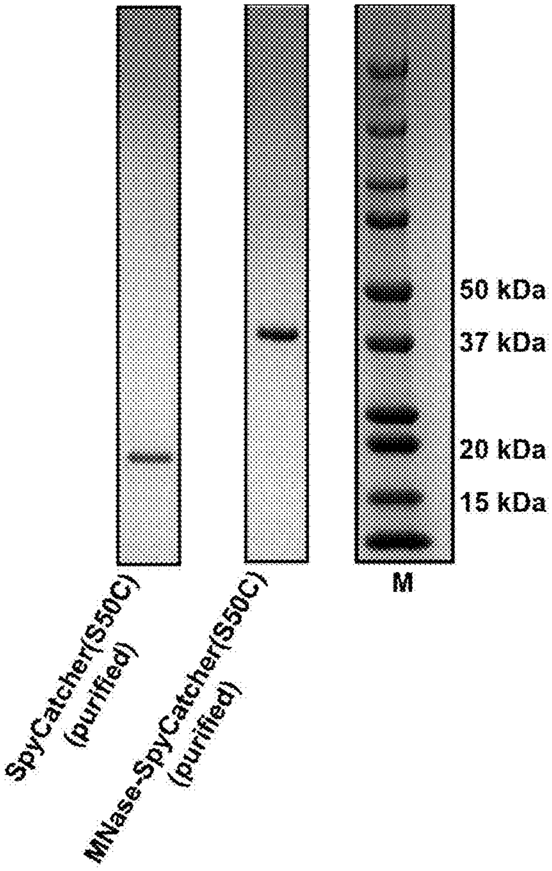
FIG. 7 shows purification of SpyCatcher002 (S50C) and MNase-SpyCatcher002 (S50C) to homogeneity with single nickel affinity purification. M=BioRad MW marker.

SpyCatcher002 (S50C) (SEQ ID NO: 7) was prepared as described in Example 1. Expression of the protein after 1 hour induction in *E. coli* is shown in FIG. 6. SpyCatcher002 (S50C) and MNase-SpyCatcher002 (S50C) (SEQ ID NO: 9) were purified to homogeneity with single nickel affinity purification (FIG. 7).

Figure 8:
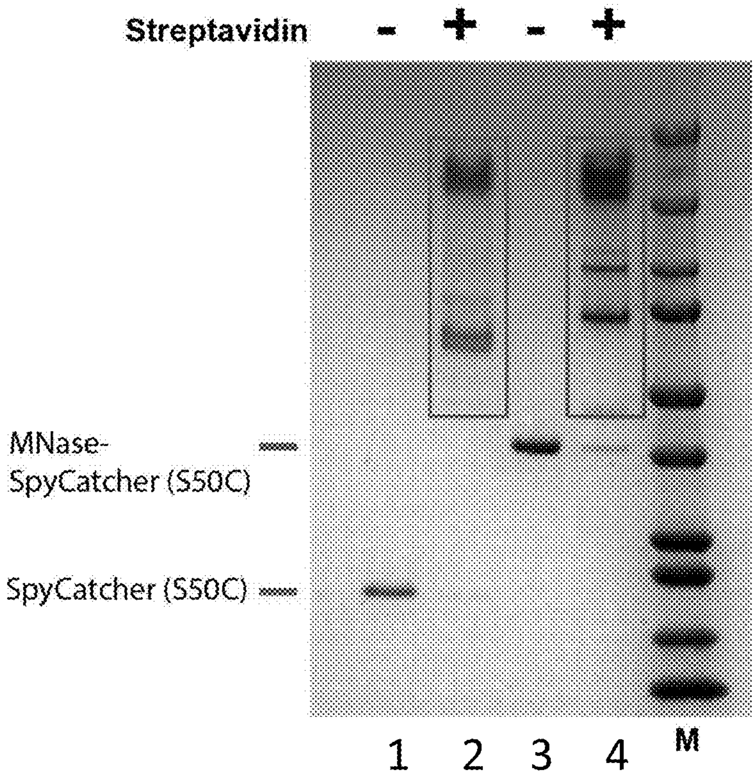
FIG. 8 shows extent of biotinylation of SpyCatcher002 (S50C) and MNase-SpyCatcher002 (S50C). Rectangles indicate complexes with streptavidin. Lanes 1 and 2, SpyCatcher002 (S50C); Lanes 3 and 4, MNase-SpyCatcher002 (S50C); M=BioRad MW marker.

The extent of biotinylation of SpyCatcher002 (S50C) and MNase-SpyCatcher002 (S50C) was assessed. As shown in FIG. 8, the approximately 90% of the proteins were biotinylated, based on the extent of unshifted SpyCatcher002 (S50C) and MNase-SpyCatcher002 (S50C) in the presence of streptavidin.

Figure 9:
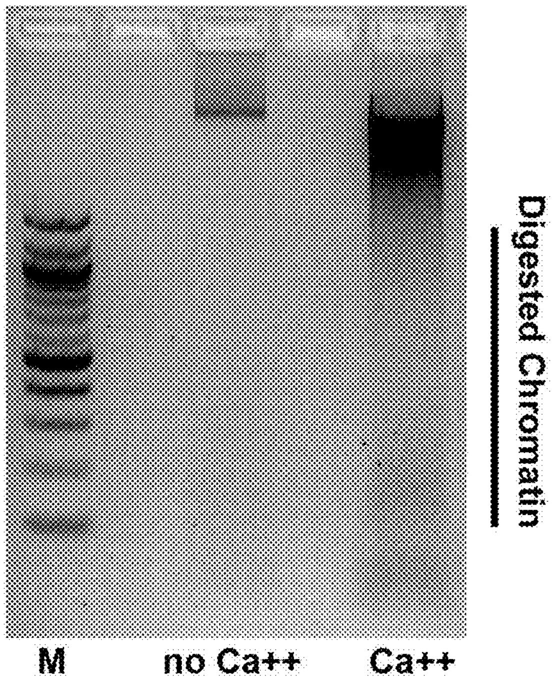
FIG. 9 shows MNase-SpyCatcher002 (S50C) entered permeabilized cells and cleaved DNA only after addition of calcium. M=100 bp MW ladder.

To assess the ability of MNase-SpyCatcher002 (S50C) to enter permeabilized cells and cleave DNA, cells were permeabilized with detergent in the presence of zymolase and MNase-SpyCatcher002 (S50C) was added for 15 minutes. Cells were washed five times with digestion buffer to remove unconjugated MNase-SpyCatcher002 (S50C). Calcium was added for 1 minute and digestion was quenched with excess EDTA/EGTA. FIG. 9 shows that MNase-SpyCatcher002 (S50C) entered permeabilized cells and cleaved DNA only after addition of calcium.

Use of MNase-SpyCatcher002 (S50C) for mapping binding of the Ume6 meiotic repressor in *S. cerevisiae* was tested. Cells (~$10^8$) containing Ume6-FLAG-SpyTag were treated with zymolase (2 mg) in the presence of MNase-SpyCatcher002 for 1 hour at 4 °C in the presence of protease inhibitors. $CaCl_2$ (1 mM) was added for 30 seconds at 4 °C and quenched with EGTA (10 mM). Total DNA was extracted by phenol/chloroform and ethanol precipitation. Small DNA fragments were enriched using Agencourt AMPURE® XP beads that remove large non-target DNA fragments leaving the small target DNA fragments in the supernatant. DNA was again ethanol precipitated and converted into sequencing libraries and sequenced by NextSeq500 paired-end sequencing. DNA fragment ends were mapped to the *S. cerevisiae* genome.

Figure 10:
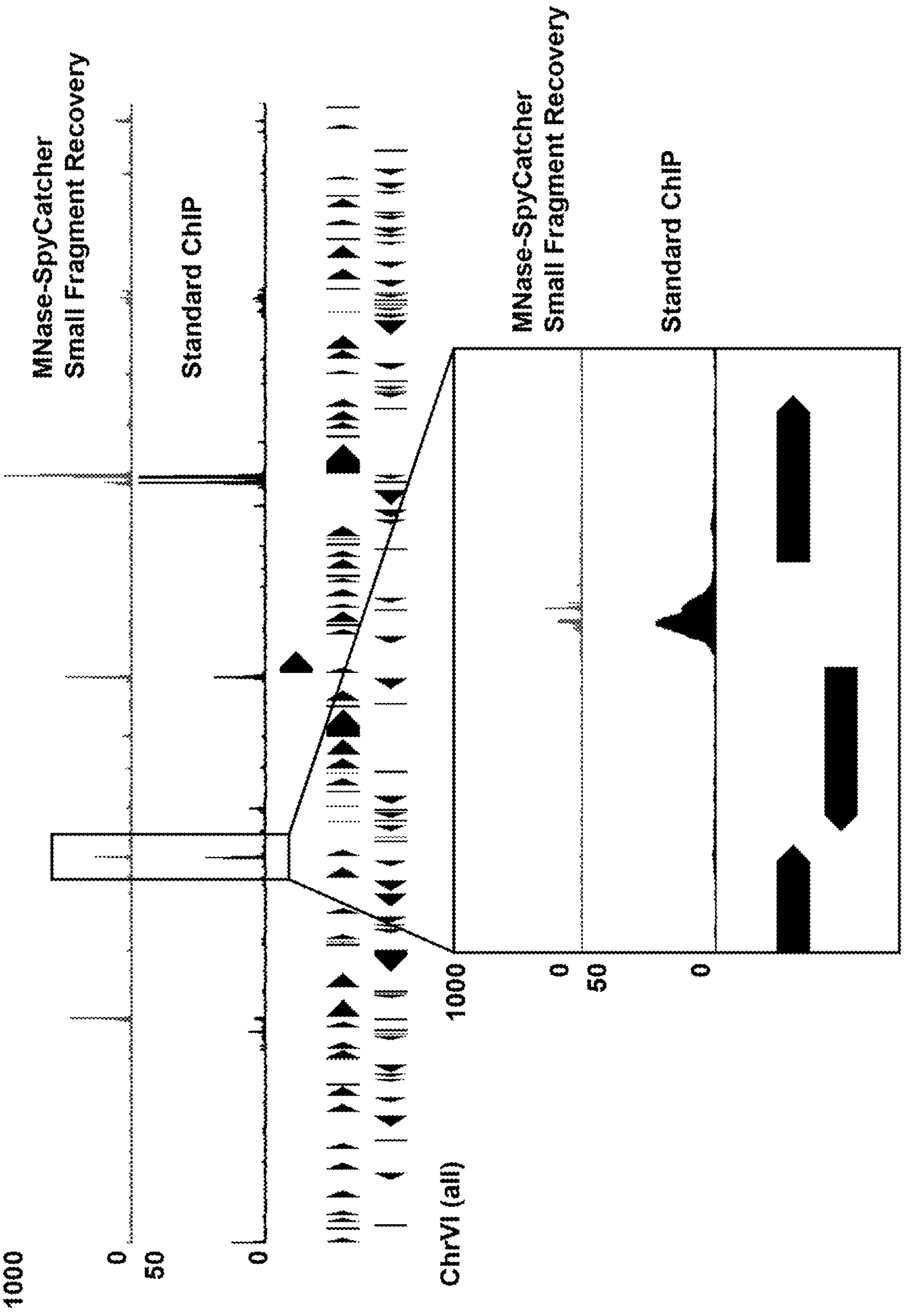
FIG. 10 shows improved signal-to-noise ratio for MNase-SpyCatcher002 (S50C) compared to standard chromatin immunoprecipitation (ChIP) for the Ume6 meiotic repressor in *S. cerevisiae*. Boxed inset shows the broad nature of ChIP peaks and narrow protection flanked by cut sites associated with MNase-SpyCatcher002 (S50C) small fragment release.
Figure 11:
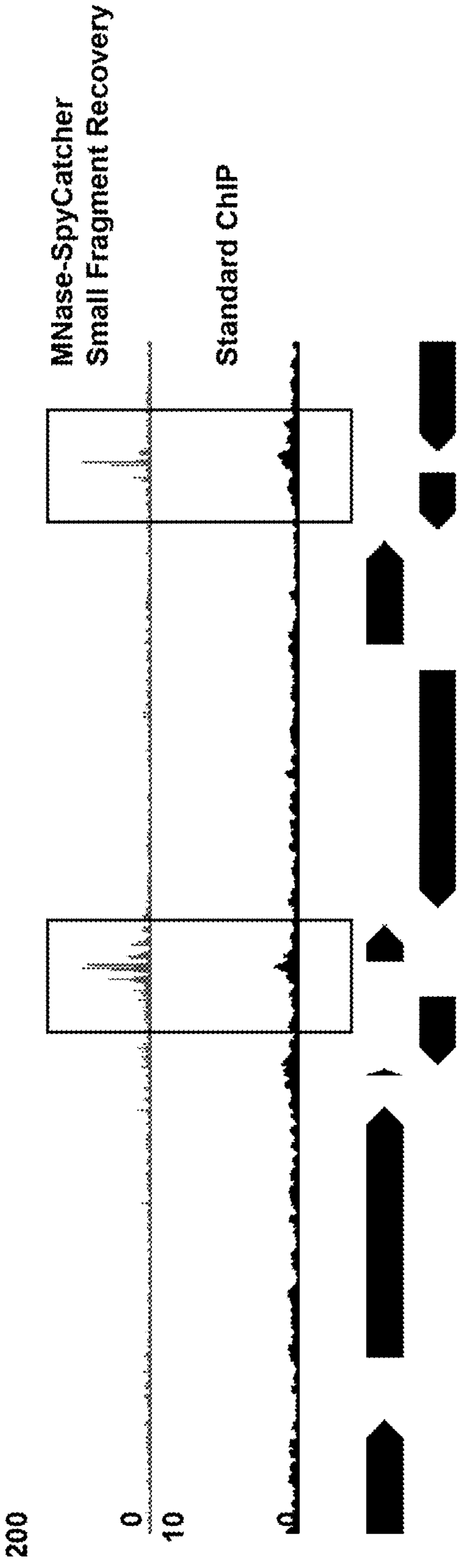
FIG. 11 shows that MNase-SpyCatcher002 (S50C) recovers additional Ume6 targets for which standard ChIP is not sensitive enough. Boxes indicate peaks that are only present in MNase-SpyCatcher002 (S50C) small fragments at sites where Ume6 binding motifs are associated.

Compared to standard chromatin immunoprecipitation (ChIP), MNase-SpyCatcher002 (S50C) exhibited improved signal-to-noise ratio (FIG. 10). MNase-SpyCatcher002 (S50C) recovered additional Ume6 targets for which standard ChIP was not sensitive enough (FIG. 11). FIGS. 12A-12C show high resolution Ume6 footprint from pooled analysis of data from all 202 intergenic Ume6 binding motifs. In comparison to MNase-SpyCatcher002 (S50C), ChIP-Seq provided diffuse and broad peaks with poor resolution (FIG. 12C).

Example 3

Protein Purification Method

Endogenous yeast Isw2, the catalytic subunit of a chromatin remodeling protein, is tagged with a SNAC-FLAG-SpyTag as described in Example 1. While FLAG will eventually be eliminated from the tagging epitope, its incorporation for this experiment allows for direct comparison of the method to standard practice. A culture is grown to mid-log phase and Isw2 is purified from half of the culture using anti-FLAG resin and FLAG peptide, while purifying Isw2 from the other half using biotin-SpyCatcher, streptavidin beads, and $Ni^{2+}$ elution. The yield of each is compared by silver stain. It is expected this strategy will capture a much greater fraction of Isw2 from the culture. Purified Isw2 from each strategy is also analyzed by mass spectrometry analysis to assess the purity of each.

Example 4

Protein Mapping—Method 1

Reb1 is tagged with a FLAG-SpyTag. While FLAG will eventually be eliminated from the tagging epitope, its incorporation for this experiment allows for direct comparison of the method to standard practice. A culture is grown to mid-log phase and Reb1 is purified from half of the culture using anti-FLAG resin and FLAG peptide, while Reb1 is purified from the other half using biotin-SpyCatcher and streptavidin beads. The time required and binding profiles are compared. The results using the SpyTag-SpyCatcher system are also compared to previously published mapping of Reb1 binding.

Example 5

Protein Mapping—Method 2

Reb1-FLAG-SpyTag culture is grown as described in Example 4. The culture is split and CUT&RUN is performed on half of the culture with FLAG primary antibody, rabbit anti-mouse secondary antibody, Protein A-MNase plus calcium to fragment nucleic acids. The other half of the culture is permeabilized and SpyCatcher-MNase is added, followed by a wash to remove unreacted SpyCatcher-MNase. Calcium is added to fragment the nucleic acids. The solubilized fragments are sequenced and compared to each other and previously published data.

Example 6

Targeted Protein Localization to Nucleic Acids

Gcn5, a histone acetyl transferase and Rpd3, a histone deacetylase, are SpyTagged. Reporter strains are created where a GFP is added at transcriptionally silent, hypoacetylated locus and RFP is added at a transcriptionally active, hyperacetylated locus. Targeting Gcn5 (but not Rpd3) to the silent locus via dCas9-SpyCatcher results in acetylating the promoter and activating GFP expression. Targeting Rpd3 (but not Gcn5) to the active gene deacetylates local chromatin and reduces RFP expression. Expression is visualized microscopically and quantified by qPCR. Local protein targeting and function are assessed using ChIP for histone acetylation (H3K23ac as a functional readout).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A method of purifying a protein, comprising:

(a) contacting:

(i) a modified SpyCatcher polypeptide comprising a cysteine at amino acid position 50 of SEQ ID NO: 6 covalently linked to a tag linked to the cysteine with (ii) a protein covalently linked to a SpyTag polypeptide or a SpyTag-sequence-specific-nickel-assisted cleavage (SNAC) tag polypeptide, under conditions sufficient for the modified SpyCatcher polypeptide and the SpyTag polypeptide or SpyTag-SNAC tag polypeptide to form a covalently bound SpyCatcher-SpyTag-protein complex or a SpyCatcher-SpyTag-SNAC tag-protein complex;

(b) contacting the SpyCatcher-SpyTag-protein complex or SpyCatcher-SpyTag-SNAC tag-protein complex with a binding partner for the tag covalently linked to the modified SpyCatcher polypeptide, under conditions sufficient for the binding partner to bind to the tag;

(c) performing one or more washes of the complex;

(d) cleaving the SpyTag or the SpyTag-SNAC tag from the complex; and (e) isolating the protein.

2. The method of claim 1, wherein the contacting the modified SpyCatcher polypeptide with the protein is performed in a lysate of a cell expressing the protein covalently linked to the SpyTag polypeptide or the SpyTag-SNAC tag polypeptide.

3. The method of claim 1, wherein the tag is biotin and the binding partner for the tag is streptavidin.

4. The method of claim 1, wherein the modified SpyCatcher polypeptide comprises an amino acid sequence having at least 95% sequence identity to SEQ ID NO: 7.

5. The method of claim 4, wherein the modified SpyCatcher polypeptide comprises the amino acid sequence of SEQ ID NO: 7.

6. The method of claim 1, wherein the SpyTag polypeptide comprises the amino acid sequence of SEQ ID NO: 1 or SEQ ID NO: 2.

7. The method of claim 1, wherein the SpyTag-SNAC tag polypeptide comprises the amino acid sequence of SEQ ID NO: 5.

* * * * *

SEQUENCE LISTING

```
<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: SpyTag sequence

<400> SEQUENCE: 1

Ala His Ile Val Met Val Asp Ala Tyr Lys Pro Thr Lys
1               5                   10


<210> SEQ ID NO 2
<211> LENGTH: 14
<212> TYPE: PRT
<213> ORGANISM: Artificial Sequence
<220> FEATURE:
<223> OTHER INFORMATION: SpyTag002 sequence

<400> SEQUENCE: 2

Val Pro Thr Ile Val Met Val Asp Ala Tyr Lys Arg Tyr Lys
1               5                   10


<210> SEQ ID NO 3
<211> LENGTH: 41
<212> TYPE: PRT
<213> ORGANISM: Artificial Sequence
<220> FEATURE:
<223> OTHER INFORMATION: 9XGGS SpyTag002 sequence

<400> SEQUENCE: 3

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Val Pro Thr Ile Val
            20                  25                  30

Met Val Asp Ala Tyr Lys Arg Tyr Lys
        35                  40


<210> SEQ ID NO 4
<211> LENGTH: 5
<212> TYPE: PRT
<213> ORGANISM: Artificial Sequence
<220> FEATURE:
<223> OTHER INFORMATION: SNAC tag sequence

<400> SEQUENCE: 4

Gly Ser His His Trp
1               5
```

<210> SEQ ID NO 5
<211> LENGTH: 22
<212> TYPE: PRT
<213> ORGANISM: Artificial Sequence
<220> FEATURE:
<223> OTHER INFORMATION: SNAC/SpyTag sequence
<220> FEATURE:
<221> NAME/KEY: REPEAT
<222> LOCATION: (6)..(8)
<223> OTHER INFORMATION: repeat = 0-9

<400> SEQUENCE: 5

```
Gly Ser His His Trp Gly Gly Ser Val Pro Thr Ile Val Met Val Asp
1               5                   10                  15

Ala Tyr Lys Arg Tyr Lys
            20
```

<210> SEQ ID NO 6
<211> LENGTH: 119
<212> TYPE: PRT
<213> ORGANISM: Artificial Sequence
<220> FEATURE:
<223> OTHER INFORMATION: SpyCatcher002 sequence

<400> SEQUENCE: 6

```
Met Val Thr Thr Leu Ser Gly Leu Ser Gly Glu Gln Gly Pro Ser Gly
1               5                   10                  15

Asp Met Thr Thr Glu Glu Asp Ser Ala Thr His Ile Lys Phe Ser Lys
            20                  25                  30

Arg Asp Glu Asp Gly Arg Glu Leu Ala Gly Ala Thr Met Glu Leu Arg
        35                  40                  45

Asp Ser Ser Gly Lys Thr Ile Ser Thr Trp Ile Ser Asp Gly His Val
    50                  55                  60

Lys Asp Phe Tyr Leu Tyr Pro Gly Lys Tyr Thr Phe Val Glu Thr Ala
65                  70                  75                  80

Ala Pro Asp Gly Tyr Glu Val Ala Thr Ala Ile Thr Phe Thr Val Asn
                85                  90                  95

Glu Gln Gly Gln Val Thr Val Asn Gly Glu Ala Thr Lys Gly Asp Ala
            100                 105                 110

His Thr Gly Ser Ser Gly Ser
        115
```

<210> SEQ ID NO 7
<211> LENGTH: 119
<212> TYPE: PRT
<213> ORGANISM: Artificial Sequence
<220> FEATURE:
<223> OTHER INFORMATION: SpyCatcher002 (S50C) sequence

<400> SEQUENCE: 7

```
Met Val Thr Thr Leu Ser Gly Leu Ser Gly Glu Gln Gly Pro Ser Gly
1               5                   10                  15

Asp Met Thr Thr Glu Glu Asp Ser Ala Thr His Ile Lys Phe Ser Lys
            20                  25                  30

Arg Asp Glu Asp Gly Arg Glu Leu Ala Gly Ala Thr Met Glu Leu Arg
        35                  40                  45

Asp Cys Ser Gly Lys Thr Ile Ser Thr Trp Ile Ser Asp Gly His Val
    50                  55                  60

Lys Asp Phe Tyr Leu Tyr Pro Gly Lys Tyr Thr Phe Val Glu Thr Ala
65                  70                  75                  80
```

Ala Pro Asp Gly Tyr Glu Val Ala Thr Ala Ile Thr Phe Thr Val Asn
85 90 95

Glu Gln Gly Gln Val Thr Val Asn Gly Glu Ala Thr Lys Gly Asp Ala
100 105 110

His Thr Gly Ser Ser Gly Ser
115

<210> SEQ ID NO 8
<211> LENGTH: 144
<212> TYPE: PRT
<213> ORGANISM: Artificial Sequence
<220> FEATURE:
<223> OTHER INFORMATION: SpyCatcher002 protein (S50C) with 6xHis tag and TEV cleavage site

<400> SEQUENCE: 8

Met Ser Tyr Tyr His His His His His His Asp Tyr Asp Ile Pro Thr
1 5 10 15

Thr Glu Asn Leu Tyr Phe Gln Gly Ala Met Val Thr Thr Leu Ser Gly
20 25 30

Leu Ser Gly Glu Gln Gly Pro Ser Gly Asp Met Thr Thr Glu Glu Asp
35 40 45

Ser Ala Thr His Ile Lys Phe Ser Lys Arg Asp Glu Asp Gly Arg Glu
50 55 60

Leu Ala Gly Ala Thr Met Glu Leu Arg Asp Cys Ser Gly Lys Thr Ile
65 70 75 80

Ser Thr Trp Ile Ser Asp Gly His Val Lys Asp Phe Tyr Leu Tyr Pro
85 90 95

Gly Lys Tyr Thr Phe Val Glu Thr Ala Ala Pro Asp Gly Tyr Glu Val
100 105 110

Ala Thr Ala Ile Thr Phe Thr Val Asn Glu Gln Gly Gln Val Thr Val
115 120 125

Asn Gly Glu Ala Thr Lys Gly Asp Ala His Thr Gly Ser Ser Gly Ser
130 135 140

<210> SEQ ID NO 9
<211> LENGTH: 309
<212> TYPE: PRT
<213> ORGANISM: Artificial Sequence
<220> FEATURE:
<223> OTHER INFORMATION: MNase-modified SpyCatcher002 (S50C) sequence

<400> SEQUENCE: 9

Met Lys His His His His His His Ser Ala Ala Thr Ser Thr Lys Lys
1 5 10 15

Leu His Lys Glu Pro Ala Thr Leu Ile Lys Ala Ile Asp Gly Asp Thr
20 25 30

Val Lys Leu Met Tyr Lys Gly Gln Pro Met Thr Phe Arg Leu Leu Leu
35 40 45

Val Asp Thr Pro Glu Thr Lys His Pro Lys Lys Gly Val Glu Lys Tyr
50 55 60

Gly Pro Glu Ala Ser Ala Phe Thr Lys Lys Met Val Glu Asn Ala Lys
65 70 75 80

Lys Ile Glu Val Glu Phe Asp Lys Gly Gln Arg Thr Asp Lys Tyr Gly
85 90 95

Arg Gly Leu Ala Tyr Ile Tyr Ala Asp Gly Lys Met Val Asn Glu Ala
100 105 110

-continued

```
Leu Val Arg Gln Gly Leu Ala Lys Val Ala Tyr Val Tyr Lys Pro Asn
        115                 120                 125

Asn Thr His Glu Gln His Leu Arg Lys Ser Glu Ala Gln Ala Lys Lys
    130                 135                 140

Glu Lys Leu Asn Ile Trp Ser Glu Asp Asn Ala Asp Ser Gly Gln Gly
145                 150                 155                 160

Gly Ser Gly Gly Ser Gly Gly Ser Gly Gly Ser Gly Gly Ser Ala Asp
                165                 170                 175

Tyr Asp Ile Pro Thr Thr Glu Asn Leu Tyr Phe Gln Gly Ala Met Val
            180                 185                 190

Thr Thr Leu Ser Gly Leu Ser Gly Glu Gln Gly Pro Ser Gly Asp Met
        195                 200                 205

Thr Thr Glu Glu Asp Ser Ala Thr His Ile Lys Phe Ser Lys Arg Asp
    210                 215                 220

Glu Asp Gly Arg Glu Leu Ala Gly Ala Thr Met Glu Leu Arg Asp Cys
225                 230                 235                 240

Ser Gly Lys Thr Ile Ser Thr Trp Ile Ser Asp Gly His Val Lys Asp
                245                 250                 255

Phe Tyr Leu Tyr Pro Gly Lys Tyr Thr Phe Val Glu Thr Ala Ala Pro
            260                 265                 270

Asp Gly Tyr Glu Val Ala Thr Ala Ile Thr Phe Thr Val Asn Glu Gln
        275                 280                 285

Gly Gln Val Thr Val Asn Gly Glu Ala Thr Lys Gly Asp Ala His Thr
    290                 295                 300

Gly Ser Ser Gly Ser
305
```

<210> SEQ ID NO 10
<211> LENGTH: 933
<212> TYPE: DNA
<213> ORGANISM: Artificial Sequence
<220> FEATURE:
<223> OTHER INFORMATION: modified SpyCatcher002(S50C) linked to micrococcal nuclease

<400> SEQUENCE: 10

```
atgaaacatc accatcacca tcactccgcg gccaccagta ccaagaagct gcacaaggag     60

cccgccaccc tgatcaaggc catagatggc gataccgtga agctgatgta taagggccag    120

cccatgacct tccgcctgct gctggtggat acccccgaga ccaagcaccc gaaaaagggc    180

gtggaaaagt acggacccga ggccagcgcc ttcacaaaaa agatggtgga gaacgccaag    240

aaaatcgagg tggagttcga taaaggccaa cgcaccgata agtatggacg cggtctagcc    300

tatatctatg ccgatggcaa aatggtgaat gaggctctgg tacggcaagg actggctaag    360

gtagcgtatg tgtataagcc taacaatacc catgagcagc acctgcgcaa gagcgaggct    420

caggcaaaga aggagaaact gaacatatgg agtgaagata atgccgacag cggtcaaggt    480

ggaagtggag gttcaggcgg ttctggtggc agtgggggaa gcgcggatta cgacatccca    540

acgaccgaaa acctgtattt tcagggcgcc atggtaacca ccttatcagg tttatcaggt    600

gagcaaggtc cgtccggtga tatgacaact gaagaagata gtgctaccca tattaaattc    660

tcaaaacgtg atgaggacgg ccgtgagtta gctggtgcaa ctatggagtt gcgtgattgc    720

tctggtaaaa ctattagtac atggatttca gatggacatg tgaaggattt ctacctgtat    780

ccaggaaaat atacatttgt cgaaaccgca gcaccagacg gttatgaggt agcaactgct    840

attaccttta cagttaatga gcaaggtcag gttactgtaa atggcgaagc aactaaaggt    900
```

gacgctcata ctggatccag tggtagctaa tag 933

<210> SEQ ID NO 11
<211> LENGTH: 10
<212> TYPE: DNA
<213> ORGANISM: Artificial Sequence
<220> FEATURE:
<223> OTHER INFORMATION: Ume6 binding motif
<220> FEATURE:
<221> NAME/KEY: misc_feature
<222> LOCATION: (2)..(2)
<223> OTHER INFORMATION: n is a, c, g, or t

<400> SEQUENCE: 11 wnggcggcww 10

<210> SEQ ID NO 12
<211> LENGTH: 6212
<212> TYPE: DNA
<213> ORGANISM: Artificial Sequence
<220> FEATURE:
<223> OTHER INFORMATION: vector encoding SpyCatcher002(S50C) covalently linked to micrococcal nuclease

<400> SEQUENCE: 12
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500

```
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
```

-continued

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgaaacatc accatcacca tcactccgcg   5100
gccaccagta ccaagaagct gcacaaggag cccgccaccc tgatcaaggc catagatggc   5160
gataccgtga agctgatgta taagggccag cccatgacct tccgcctgct gctggtggat   5220
acccccgaga ccaagcaccc gaaaaagggc gtggaaaagt acggacccga ggccagcgcc   5280
ttcacaaaaa agatggtgga gaacgccaag aaaatcgagg tggagttcga taaaggccaa   5340
cgcaccgata agtatggacg cggtctagcc tatatctatg ccgatggcaa aatggtgaat   5400
gaggctctgg tacggcaagg actggctaag gtagcgtatg tgtataagcc taacaatacc   5460
catgagcagc acctgcgcaa gagcgaggct caggcaaaga aggagaaact gaacatatgg   5520
agtgaagata atgccgacag cggtcaaggt ggaagtggag gttcaggcgg ttctggtggc   5580
agtgggggaa gcgcggatta cgacatccca acgaccgaaa acctgtattt tcagggcgcc   5640
atggtaacca ccttatcagg tttatcaggt gagcaaggtc cgtccggtga tatgacaact   5700
gaagaagata gtgctaccca tattaaattc tcaaaacgtg atgaggacgg ccgtgagtta   5760
gctggtgcaa ctatggagtt gcgtgattgc tctggtaaaa ctattagtac atggatttca   5820
gatggacatg tgaaggattt ctacctgtat ccaggaaaat atacatttgt cgaaaccgca   5880
gcaccagacg gttatgaggt agcaactgct attaccttta cagttaatga gcaaggtcag   5940
gttactgtaa atggcgaagc aactaaaggt gacgctcata ctggatccag tggtagctaa   6000
tagggtaccg gatccgaatt cgagctccgt cgacaagctt gcggccgcac tcgagcacca   6060
ccaccaccac cactgagatc cggctgctaa caaagcccga aaggaagctg agttggctgc   6120
tgccaccgct gagcaataac tagcataacc ccttggggcc tctaaacggg tcttgagggg   6180
tttttgctg aaaggaggaa ctatatccgg at                                 6212
```

-continued

```
<210> SEQ ID NO 13
<211> LENGTH: 363
<212> TYPE: DNA
<213> ORGANISM: Artificial Sequence
<220> FEATURE:
<223> OTHER INFORMATION: SpyCatcher002(S50C)

<400> SEQUENCE: 13

atggtaacca ccttatcagg tttatcaggt gagcaaggtc cgtccggtga tatgacaact     60

gaagaagata gtgctaccca tattaaattc tcaaaacgtg atgaggacgg ccgtgagtta    120

gctggtgcaa ctatggagtt gcgtgattgc tctggtaaaa ctattagtac atggatttca    180

gatggacatg tgaaggattt ctacctgtat ccaggaaaat atacatttgt cgaaaccgca    240

gcaccagacg gttatgaggt agcaactgct attaccttta cagttaatga gcaaggtcag    300

gttactgtaa atggcgaagc aactaaaggt gacgctcata ctggatccag tggtagctaa    360

tag                                                                  363
```